United States Patent [19]
Gozani et al.

[11] Patent Number: 6,132,386
[45] Date of Patent: Oct. 17, 2000

[54] METHODS FOR THE ASSESSMENT OF NEUROMUSCULAR FUNCTION BY F-WAVE LATENCY

[75] Inventors: Shai N. Gozani, Brookline; Matthew A. Neimark, Somerville, both of Mass.

[73] Assignee: Neurometrix, Inc., Cambridge, Mass.

[21] Appl. No.: 09/270,550

[22] Filed: Mar. 16, 1999

Related U.S. Application Data

[60] Continuation-in-part of application No. 09/022,990, Feb. 12, 1998, Pat. No. 5,976,094, which is a division of application No. 08/886,861, Jul. 1, 1997, Pat. No. 5,851,191.

[51] Int. Cl.[7] ................................................ A67B 5/05
[52] U.S. Cl. ............................................................ 600/554
[58] Field of Search .................................. 600/483, 546, 600/554

[56] References Cited

U.S. PATENT DOCUMENTS

| | | | |
|---|---|---|---|
| 3,886,931 | 6/1975 | Rodler | 128/2.1 R |
| 4,807,643 | 2/1989 | Rosier | 128/741 |
| 5,050,612 | 9/1991 | Matsumura | 128/670 |
| 5,080,099 | 1/1992 | Way et al. | 128/640 |
| 5,092,344 | 3/1992 | Lee | 128/741 |
| 5,099,844 | 3/1992 | Faupel | 128/653.1 |
| 5,131,401 | 7/1992 | Westenskow et al. | 128/741 |
| 5,143,081 | 9/1992 | Young et al. | 128/741 |
| 5,203,330 | 4/1993 | Schaefer et al. | 128/640 |
| 5,215,100 | 6/1993 | Spitz et al. | 128/741 |
| 5,255,677 | 10/1993 | Schaefer et al. | 128/640 |
| 5,327,902 | 7/1994 | Lemmen | 128/734 |
| 5,333,618 | 8/1994 | Lekhtman et al. | 128/734 |
| 5,379,764 | 1/1995 | Barnes et al. | 128/633 |
| 5,466,256 | 11/1995 | McAdams et al. | 607/142 |
| 5,467,768 | 11/1995 | Suda et al. | 128/640 |
| 5,496,363 | 3/1996 | Burgio et al. | 607/152 |
| 5,511,553 | 4/1996 | Segalowitz | 128/696 |
| 5,560,372 | 10/1996 | Cory | 128/741 |

FOREIGN PATENT DOCUMENTS

| | | |
|---|---|---|
| 0 025 222 A2 | 3/1981 | European Pat. Off. . |
| 0 436 121 A1 | 7/1991 | European Pat. Off. . |
| WO 91/16001 | 10/1991 | WIPO . |
| WO 92/03974 | 3/1992 | WIPO . |

OTHER PUBLICATIONS

Testerman, Roy, "Method of Measuring Blood Glucose Level by Sensing Evoked Action Potentials in Peripheral Nerve," Research Disclosure, 227:92, Article No. 22728 (Mar. 1983).

Oh, Shin J., M.D., "Clinical Electromyography: Nerve Conduction Studies," (Williams & Wilkins, 2nd Ed., 1993).

Gilliatt, R.W. and Willison, R.G., "The Refractory and Supernormal Periods of the Human Median Nerve," (*J. Neurol. Neurosurg. Psychiat.*, 2:1963), pp. 136–147.

Lindstrom, P. and Brismar, T., "Mechanism of Anoxic Conduction Block in Mammalian Nerve," (*Acta Physiol Scand*, 141:1991), pp. 429–433.

Basmajian, John V. M.D., and De Luca, Carlo J., Ph.D., "Muscles Alive: Their Functions Revealed by Electromyography," (Williams & Wilkins, 5th Ed., 1995).

Fujisawa, M., D.D.S. et al., "Surface Electromyographic Electrode Pair With Built–In Buffer–Amplifiers," (*The Journal of Prosthetic Dentistry*, vol. 63, No. 3, Mar. 1990), pp. 350–352.

Seneviratne, K.N. and Peiris, O.A., "The Effect of Ischaemia on the Excitability of Human Sensory Nerve," (*J. Neurol. Neurosurg. Psychiat.*, 31:1968), pp. 338–347.

(List continued on next page.)

*Primary Examiner*—William E. Kamm
*Attorney, Agent, or Firm*—Testa, Hurwitz & Thibeault, LLP

[57] ABSTRACT

Methods are provided for the assessment of neuromuscular function by F-wave latency. Stimuli are applied to a nerve that traverses a wrist or an ankle joint of an individual. Stimulation of the nerve causes a muscle innervated by that nerve to respond, thereby generating a myoelectric potential. One component of the myoelectric potential is the F-wave component. The F-wave latency between application of the stimulus and the detection of the myoelectric potential is used to provide an assessment of a neuromuscular function of the nerve and/or muscle.

54 Claims, 12 Drawing Sheets

OTHER PUBLICATIONS

Shefner, Jeremy M. M.D., "The Use of Sensory Action Potentials in the Diagnosis of Peripheral Nerve Disease," (Arch Neurol–vol. 47, Mar. 1990); pp. 341–348.

Brodie, Chaya and Sampson, S.R., "Contribution of Electrogenic Sodium–Potassium ATPase to Resting Membrane Potential of Cultured Rat Skeletal Myotubes," (*Brain Research*, 347:1985), pp. 28–35.

Stewart, Mark A., et al., "Substrate Changes in Peripheral Nerve During Ischaemia and Wallerian Degeneration," (*Journal of Neurochemistry*, vol. 12, 1965), pp. 719–727.

Bostock, H., et al., "Changes in Excitability and Accommodation of Human Motor Axons Following Brief Periods of Ischaemia," (*Journal of Physiology*, 441: 1991 Great Britain), pp. 513–535.

Nishimura, Suzushi, et al., "Clinical Application of an Active Electrode Using an Operational Amplifier," (*IEEE Transactions on Biomedical Engineering*, vol. 39, No. 10, Oct. 1992), pp. 1096–1099.

http://www.asoi.com/neumed/overview.html.

http://www.cs.msstate.edu/~csmith/biomech/nrvecond.html.

http://www.aosi.com/neumed/p.html.

http://www.netspace.org/~simon/Pictures.html#NCV.

"Now Diagnose and Monitor the Clinical Progress of Compression Neuropathies Such as Carpal Tunnel Syndrome—in the Office or Clinic", *Neuroton Medical*, Lawrenceville NJ (product literature) (1991).

METHODS FOR THE ASSESSMENT OF NEUROMUSCULAR FUNCTION BY F-WAVE LATENCY

CROSS-REFERENCE TO RELATED APPLICATIONS

The present application is a continuation-in-part of U.S. Ser. No. 09/022,990, filed Feb. 12, 1998, and now U.S. Pat. No. 5,976,094, which is a divisional of U.S. Ser. No. 08/886,861, filed Jul. 1, 1997 and now U.S. Pat. No. 5,851,191, both of which are hereby incorporated by reference.

FIELD OF THE INVENTION

The invention relates to apparatus and methods for assessment of neuromuscular function. More specifically, the invention relates to apparatus and methods for diagnosing peripheral nerve and muscle pathologies based on assessments of neuromuscular function.

BACKGROUND OF THE INVENTION

There are many clinical and non-clinical situations that call for rapid, reliable and low-cost assessments of neuromuscular function. Reliable and automated devices are needed to monitor neuromuscular function in surgical and intensive care settings. For example, muscle relaxants significantly improve surgical procedures and post-operative care by regulating the efficacy of nerve to muscle coupling through a process called neuromuscular blockade. They are, however, difficult to use in a safe and effective manner because of the wide variation and lack of predictability of patient responses to them. In another setting, an easy to use and reliable indicator would be beneficial in assessing potential contamination exposure situations by chemical agents. These agents disrupt neuromuscular function and effectively cause neuromuscular blockage, putting soldiers and civilians at risk.

The most common causes of neuromuscular disruption are, however, related to pathologies of the peripheral nerves and muscles. Neuromuscular disorders, such as, for example, Carpal Tunnel Syndrome (CTS), diabetic neuropathy, and toxic neuropathy, are very common and well known to the general public. Detection of such disorders involves determining the speed with which a nerve that is believed to be affected transmits a signal. One way to make such a determination involves stimulating a nerve that innervates a muscle, and then determining a delay between the onset of the stimulation and the muscle's response. The muscle response typically has two components, namely the M-wave component and the F-wave component. Detection and analysis of either of these two components of the muscle response provides information on the presence or absence of a neuromuscular pathology. Despite their extensive impact on individuals and the health care system, however, detection and monitoring of such neuromuscular pathologies remains expensive, complicated, and highly underutilized.

CTS is one of the most common forms of neuromuscular disease. The disease is thought to arise from compression of the median nerve as it traverses the wrist. CTS often causes discomfort or loss of sensation in the hand, and, in severe cases, a nearly complete inability to use one's hands. Highly repetitive wrist movements, as well as certain medical conditions, such as, for example, diabetes, rheumatoid arthritis, thyroid disease, and pregnancy, are thought to be factors that contribute to the onset of CTS. In 1995, the US National Center for Health Statistics estimated that there were over 1.89 million cases of CTS in the United States alone.

Effective prevention of CTS and other nervous system pathologies requires early detection and subsequent action. Unfortunately, the state of CTS diagnosis is rather poor. Even experienced physicians find it difficult to diagnose and stage the severity of CTS based on symptoms alone. The only objective way to detect CTS is to measure the transmission of neural signals across the wrist. The gold standard approach is a formal nerve conduction study by a clinical neurologist, but this clinical procedure has a number of important disadvantages. First, it is a time consuming process that requires the services of a medical expert, such as a neurologist. Second, the procedure is very costly (e.g., $600–$1000). Furthermore, it is not available in environments where early detection could significantly decrease the rate of CTS, such as the workplace where a significant number of causes of CTS appear. As a result of these disadvantages, formal electrophysiological evaluation of suspected CTS is used relatively infrequently, which decreases the likelihood of early detection and prevention.

The prior art reveals a number of attempts to simplify the assessment of neuromuscular function, such as in diagnosing CTS, and to make such diagnostic measurements available to non-experts. Rosier (U.S. Pat. No. 4,807,643) describes a portable device for measuring nerve conduction velocity in patients. This instrument has, however, several very important disadvantages. First, it requires placement of two sets of electrodes: one set at the stimulation site and one set at the detection site. Consequently, a skilled operator with a fairly sophisticated knowledge of nerve and muscle anatomy must ensure correct application of the device. Inappropriate placement of one or both of the electrode sets can lead to significant diagnostic errors. Second, the Rosier apparatus suffers from the disadvantage that it is not automated. In particular, it demands that the user of the device establish the magnitude of the electrical stimulus, as well as a response detection threshold. These parameters are difficult to determine a priori, and their rapid and correct establishment requires an advanced understanding of both neurophysiology and the detailed electronic operation of the apparatus.

Spitz, et al. (U.S. Pat. No. 5,215,100) and Lemmen (U.S. Pat. No. 5,327,902) have also attempted to enhance the earlier prior art. Specifically, they proposed systems that measure nerve conduction parameters between the arm or forearm and the hand, such as would be required for diagnosing CTS. In both cases, however, electrode supporting structures or fixtures were proposed that would substantially fix the positions at which the stimulation electrodes contact the arm and the detection electrodes contact the hand. Furthermore, these systems suffer, from several important disadvantages. First, both systems are rather large and bulky, because they include a supporting fixture for the arm and hand of an adult. This severely limits their portability and increases their cost. Second, these devices still require highly trained operators who can make the appropriate adjustments on the apparatus so as to insure electrode contact with the proper anatomical sites on the arm and hand. A third disadvantage of both systems is that they continue to demand multiple operator decisions regarding stimulation and detection parameters. Finally, these prior art systems suffer from the disadvantage that they do not automatically implement the diagnostic procedure and indicate the results in a simple and readily interpretable form.

There remains a need, therefore, for apparatus and methods for assessing neuromuscular function that are less time consuming, less expensive, and more available to a wider range of the general public (i.e., are more portable and easy to use). Such apparatus and methods are needed to provide more widespread early detection and prevention of neuromuscular pathologies, such as CTS, diabetic neuropathy, and toxic neuropathy. The present invention addresses these needs.

SUMMARY OF THE INVENTION

In accordance with the invention, apparatus and methods are provided for the substantially automated, rapid, and efficient assessment of neuromuscular function without the involvement of highly trained personnel. Assessment of neuromuscular function occurs by stimulating a nerve, then measuring the response of a muscle innervated by that nerve. The muscle response is detected by measuring the myoelectric potential generated by the muscle in response to the stimulus. One indication of the physiological state of the nerve is provided by the delay between application of a stimulus and detection of a muscular response. If the nerve is damaged, conduction of the signal via the nerve to the muscle, and, hence, detection of the muscle's response, will be slower than in a healthy nerve. An abnormally high delay between stimulus application and detection of muscle response indicates, therefore, impaired neuromuscular function.

Other indications of a physiological function of a nerve are provided by the F-wave latency between application of a stimulus and detection of a myoelectric response and by the conduction velocity of the nerve. F-wave latencies account for the time that is required for the impulse generated by the nerve as a result of the stimulus to propagate through the spinal cord of the individual before being conducted to the muscle. A conduction velocity is determined by stimulating the nerve at at least two different locations, measuring the delays as a result of these stimulations, calculating the difference between the delays, determining the distance between the at least two stimulation locations, and then dividing the distance by the difference between the delays.

In apparatus and methods of the invention, both the application of stimulus and the detection of responses is carried out entirely at a position that is immediately proximal to the wrist of an individual (i.e., the wrist crease). In an alternative embodiment of the invention, both the application of stimulus and the detection of responses is carried out entirely at a position that is at or proximal to the ankle joint. These anatomical locations are familiar and easy to locate, thus ensuring correct placement of the apparatus at the assessment site by non-experts while still maintaining the accuracy of results. This ease of use increases the availability and decreases the cost of diagnosing pathologies such as Carpal Tunnel Syndrome (CTS) and diabetic neuropathy, respectively.

Apparatus and methods of the invention assess neuromuscular function in the arm of an individual by using a stimulator to apply a stimulus to a nerve that traverses the wrist of the individual. The stimulator is adapted for applying the stimulus to the nerve at a position which is proximal to the wrist of the individual. The stimulus may be, for example, an electrical stimulus or a magnetic stimulus. Other types of stimuli may be used. A detector, adapted for detecting the myoelectric potential generated by a muscle in response to the stimulus, detects the response of the muscle to the stimulus at a site that is also proximal to the wrist of the individual. A controller then evaluates the physiological function of the nerve by, for example, determining a delay between application of stimulus and detection of myoelectric potential. The delay is then correlated to the presence or absence of a neuromuscular pathology, such as, for example, CTS.

In another embodiment, apparatus and methods of the invention assess neuromuscular function in the leg and foot of an individual by using a stimulator to apply a stimulus to a nerve that traverses the ankle joint of the individual. The stimulator is adapted for applying the stimulus to the nerve at one or more positions which are proximal to the ankle joint of the individual. A detector, adapted for detecting the myoelectric potential generated by a muscle in response to the stimulus, detects the response of the muscle to the stimulus at a site that is also proximal to the ankle joint of the individual. A controller then evaluates the physiological function of the nerve by, for example, determining a conduction velocity between two stimulation sites proximal to the ankle joint. The conduction velocity is then correlated to the presence or absence of a neuromuscular pathology, such as, for example, diabetic neuropathy.

In a preferred embodiment, the stimulator and the detector are both in electrical communication with electrodes adapted for placement on the arm of an individual proximal to the wrist. In an alternative embodiment, the electrodes are adapted for placement on the leg of an individual proximal to the ankle joint. The controller may also be in electrical communication with a reference electrode and a temperature sensor. An apparatus of the invention may further comprise a communications port for establishing communication between the apparatus and an external device, such as, for example, a personal computer, a printer, a modem, or the Internet.

In another embodiment, an apparatus of the invention further comprises an indicator. The indicator is in electrical communication with the controller and is adapted for indicating the physiological function evaluated by the controller in response to the stimulus applied and myoelectric potential detected. The indicator may comprise a light emitting diode or a liquid crystal display. In a particularly preferred embodiment, the indicator is adapted for indicating the presence or absence of CTS. In other embodiments, the indicator is adapted for indicating other physiological functions of a peripheral nervous system of an individual, such as F-wave latencies or diabetic neuropathies, for example.

An apparatus of the invention may be further embodied in an electrode configuration contained in an electrode housing for releasably securing to the wrist of an individual. The electrode housing contains an attachment mechanism, such as, for example, a non-irritating adhesive material, for securing to the arm of the individual and may be disposable. The electrode housing preferably has a connector for electrical communication with an apparatus comprising a stimulator, a detector, and a processor, as described above.

The electrode housing comprises stimulation and detection electrodes. The stimulation and detection electrodes are sized and shaped in the housing so that they contact an anterior aspect of an arm of the individual proximal to the wrist, when the housing is secured to the wrist of the individual. The electrode configuration may further contain a temperature sensor and/or a reference electrode.

In a preferred embodiment, the electrode configuration comprises a second stimulation electrode and a second detection electrode. The two stimulation electrodes are positioned substantially in the center of the electrode housing and are arranged so that they are positioned at opposite ends of the housing. The two stimulation electrodes are preferably arranged so that, when the housing is placed on the anterior aspect of an arm of a user, one of the stimulation electrodes is located immediately proximal to the wrist and the other at a location more proximal from the wrist. The two detection electrodes are also located at opposite ends of the housing, but they are positioned such that, when placed on the anterior aspect of an arm of a user, one detection electrode is located on the medial, and the other on the lateral, side of the wrist.

In another embodiment of the invention a neuromuscular electrode is provided. A neuromuscular electrode for the assessment of a physiological function of a peripheral nerve and/or a muscle in communication with that nerve includes a stimulation site, a detection site, and a data memory. The stimulation site is adapted for producing a stimulus and for applying that stimulus to a nerve of an individual. The detection site may be in a fixed relationship with respect to the stimulation site and is adapted for detecting a bioelectric potential. The bioelectric potential is generated by a muscle or nerve in communication with the stimulated nerve in response to the stimulus. The bioelectric potential may be a myoelectric potential generated by a muscle in communication with the stimulated nerve. The data memory is adapted for storing a signal representative of a characteristic of the neuromuscular electrode. A neuromuscular electrode of the invention is used to evaluate a physiological function of the nerve and/or the muscle in response to the stimulus, the bioelectric potential, and the characteristic.

A characteristic of the neuromuscular electrode may include the height of the patient that is associated with the size of the neuromuscular electrode, a serial number of the neuromuscular electrode, an indication that the neuromuscular electrode has been used on an individual, or an indication that the neuromuscular electrode has not been used on an individual. The neuromuscular electrode may come in sizes, such as small, medium, or large, for example. For each size, a height of an individual may be included in the data memory of the neuromuscular electrode. This height is later used to adjust determination of a physiological function based on the height of the individual. An indication that a neuromuscular electrode of the invention has been used on an individual may include an electronic flag in the data memory. The presence of said flag may indicate that the neuromuscular electrode has been used to make physiological determinations and that it may not be used again.

A neuromuscular electrode system includes a neuromuscular electrode, as described above, and a controller in electrical communication with the data memory, the stimulation site, and the detection site for determining whether the electrode has been used based on the signal representative of an indication of use in the data memory. In one embodiment, the controller comprises a data processor for processing this signal to determine if the neuromuscular electrode has been used. The data processor and the controller may be embodied as a single microprocessor. The controller directs the stimulation site to stimulate the nerve if a determination that the neuromuscular electrode has not been used is made and processes the bioelectric potential and stimulus. The controller then correlates the processing results to a physiological function of the nerve and/or muscle. The physiological function may include a delay between application of the stimulus and detection of the bioelectric potential, a F-wave latency between application of the stimulus and detection of the bioelectric potential, a conduction velocity of the nerve, or an amplitude of the bioelectric potential. The physiological function may be modified by the controller as a function of the height of the individual, which is encoded in the data memory, as described above, or by the temperature of the skin of the individual, as measured by a temperature sensor, which is also in electrical communication with the controller.

A controller of a neuromuscular electrode system of the invention is adapted for generating a deactivation signal upon detection of certain specific signals and for transmitting that deactivation signal to the data memory. Upon receiving the deactivation signal, the signal representative of an indication of use of the neuromuscular electrode is modified. This modification may include the generation of an electronic flag in the data memory.

The specific signal changes that cause the controller to generate a deactivation signal include, but are not limited to, detection of an impedance of skin that exceeds a predetermined value. The controller further monitors an impedance of skin of the individual and generates a deactivation signal upon detection of an impedance of skin that exceeds a predetermined value. The controller then transmits the deactivation signal to the data memory. Another specific signal change includes a predetermined change in the bioelectric potential. The controller monitors the bioelectric potential and generates a deactivation signal upon detection of a predetermined change in the bioelectric potential and transmits that deactivation signal to the data memory. Finally, the data memory may contain a unique serial number of the neuromuscular electrode. The controller also compares the bioelectric potential to at least one bioelectric potential previously determined by the neuromuscular electrode having that unique serial number. If the controller detects a predetermined characteristic change between the bioelectric potential and the at least one previously determined bioelectric potential for the neuromuscular electrode having that unique serial number, the controller generates a deactivation signal and transmits that deactivation signal to the data memory. In other embodiments, the unique serial number is used to match the physiological function with the individual.

Methods of the invention relate to the assessment of neuromuscular function using an apparatus of the invention. Using an apparatus, as described above, a stimulus is applied to a nerve that traverses the wrist of an individual proximal to the wrist. Alternatively, a stimulus is applied proximal to a nerve that traverses the ankle joint of an individual. A muscle innervated by the nerve responds and thereby generates a myoelectric potential, which is detected proximal to the wrist of the individual. The detected response is processed by determining a first derivative of the myoelectric potential and, preferably, a second derivative of the myoelectric potential. In a preferred embodiment, these derivatives are used to determine an appropriate stimulation level, as well as to determine the delay between application of stimuli and detection of the associated responses. In another embodiment, additional measurements related to the delay are taken. For example, changes in the delay induced by application of at least two stimulus applications is determined. The delay and associated parameters calculated from any of the measurements are then correlated to a physiological function of the nerve and muscle.

In preferred embodiments, an apparatus of the invention is used to indicate the presence or absence of CTS. A plurality of stimuli are applied to a nerve passing through the carpal tunnel, such as, for example, the median nerve. The stimuli may be delivered one at a time at a predetermined rate or they may be delivered in pairs at a predetermined rate. If delivered in pairs, the application of stimuli is separated by a predetermined time interval. In another embodiment, an apparatus of the invention is used to indicate the presence or absence diabetic neuropathy. In this embodiment, a plurality of stimuli are applied to a nerve passing through the ankle joint, such as, for example, the peroneal nerve.

A plurality of myoelectric potentials are generated by a muscle innervated by the stimulated nerve in response to the stimuli. Each myoelectric potential is generated in response to a respective stimulus application. A delay for each of said stimulus applications and detected responses is determined. Statistics such as, for example, mean and standard deviation, are calculated for the plurality of delays. The probable value that the individual has CTS or diabetic neuropathy is calculated based on these statistics. An indication of the presence or absence of CTS or diabetic neuropathy is then given based on that value.

In other embodiments of the invention, the method may involve further steps. For example, in one embodiment of the invention, the method relates to calculating the difference between delays measured in response to two stimuli delivered at short temporal intervals, and determining the probable value that an individual has CTS or diabetic neuropathy based on these delay differences and calculated statistics, as described above. In another embodiment, a level of noise is measured prior to stimulating the nerve. In yet another embodiment, the mean and standard deviation of the delays is adjusted relative to the skin temperature.

An apparatus and method for the essentially automated and accurate assessment of neuromuscular function is therefore provided. The apparatus and methods of the invention allow for the less costly and more readily available detection of neuromuscular pathologies, such as, for example, CTS or diabetic neuropathy, without the aid of a skilled professional.

The invention will be understood further upon consideration of the following drawings, description, and claims.

DETAILED DESCRIPTION OF THE INVENTION

The present invention offers a detection and monitoring system for peripheral neurological conditions, such as Carpal Tunnel Syndrome, diabetic neuropathy, and toxic neuropathies, that is less time consuming, less expensive, and more available to a wider range of the general public than existing systems. One of the most effective ways to detect peripheral neuropathies is to monitor the response of a motor nerve to stimulation.

A motor nerve response signal typically consists of two components, namely the M-wave component and the F-wave component. The M-wave component is generally quantified by the distal motor latency (DML). The DML is generally defined as the amount of time that elapses between the start of the stimulus (i.e., time=0) and the initial negative deflection of the M-wave component of the muscle response signal (i.e., myoelectric potential). The F-wave component of the muscle response signal, on the other hand, is typically quantified by the minimum or median F-wave latency. The F-wave latency represents the time lag between stimulation of a motor nerve and arrival of the neurally conducted impulse at the muscle group innervated by that nerve after antidromic propagation of the impulse to the spinal cord, reflection of the impulse in the anterior horn cells of the spinal cord, and then orthodromic conduction back down the motor nerve.

F-waves differ from M-waves in a number of important ways that impact their analysis and diagnostic use. First, F-waves are typically 25–50 times smaller than M-waves. Second, unlike M-waves, which are evoked by every stimulus, F-waves are probabilistic, and may or may not be generated for a given stimulus. Also, F-waves evoked by different but equivalent stimuli may consist of different morphologies and have different latencies. Consequently, a statistical characterization of the ensemble of F-wave latencies, such as the minimum, mean, or median, is typically reported.

Figure 1A:
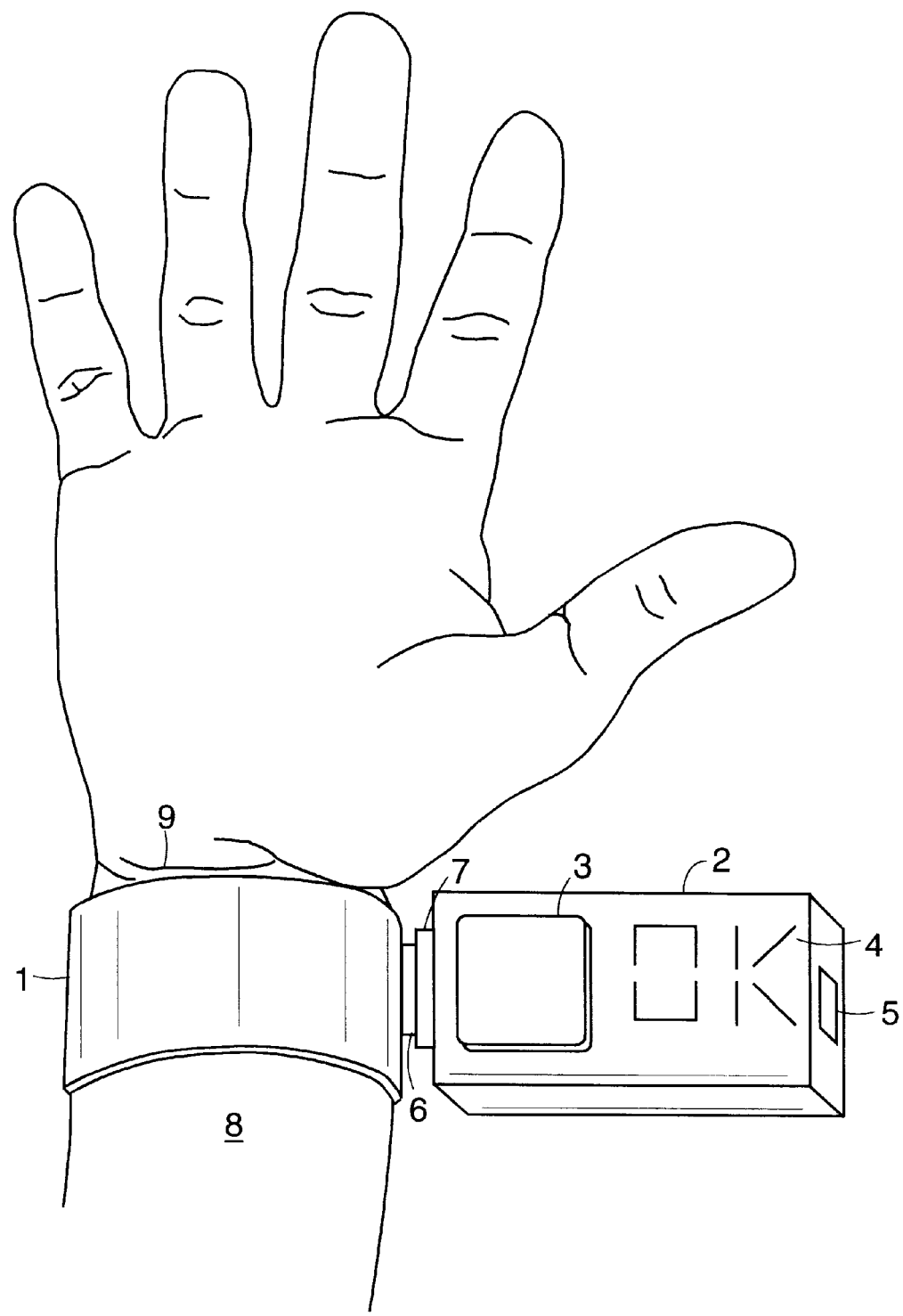
FIG. 1A is an illustration of an embodiment of the apparatus of the invention attached to the wrist of a user.

An illustrative embodiment of an apparatus of the invention and its placement on the user's forearm 8 is shown in FIG. 1A. The invention consists of two major components: a neuromuscular electrode 1 and an electronic monitor 2. The neuromuscular electrode 1 includes both a stimulator and a detector. The electronic monitor 2 includes both a controller and an indicator. In this embodiment, the neuromuscular electrode 1 and electronic monitor 2 are physically separable with electrical connections between the two components established by physical contact between a connector 6, associated with the neuromuscular electrode 1 and connector slot 7 associated with the electronic monitor 2. In another embodiment, neuromuscular electrode 1 and electronic monitor 2 constitute a single, physically inseparable unit. The electronic monitor 2 contains means to actuate the diagnostic process. Referring to the illustrative embodiment shown in FIG. 1A, a push-button 3 is provided to initiate said diagnostic process. The electronic monitor 2 also contains an indicator to display or convey the results of the diagnostic process. Referring to the illustrative embodiment shown in FIG. 1A, an indicator includes a display 4, which includes two multi-segment light-emitting diodes (LEDs) and which provides feedback and results. Other indicators may be used, including, but not limited to, single and multicolor discrete LEDs. Other types of indicators, such as, for example, speakers, may provide auditory signals. The electronic monitor 2 also contains a communications port to connect and communicate with external devices. Referring to the illustrative embodiment shown in FIG. 1A, the communications port includes a jack 5 into which a cable may be inserted. The other end of the cable is then connected to any number of different devices, including, but not limited to, computers and telephone lines.

Figure 1B:
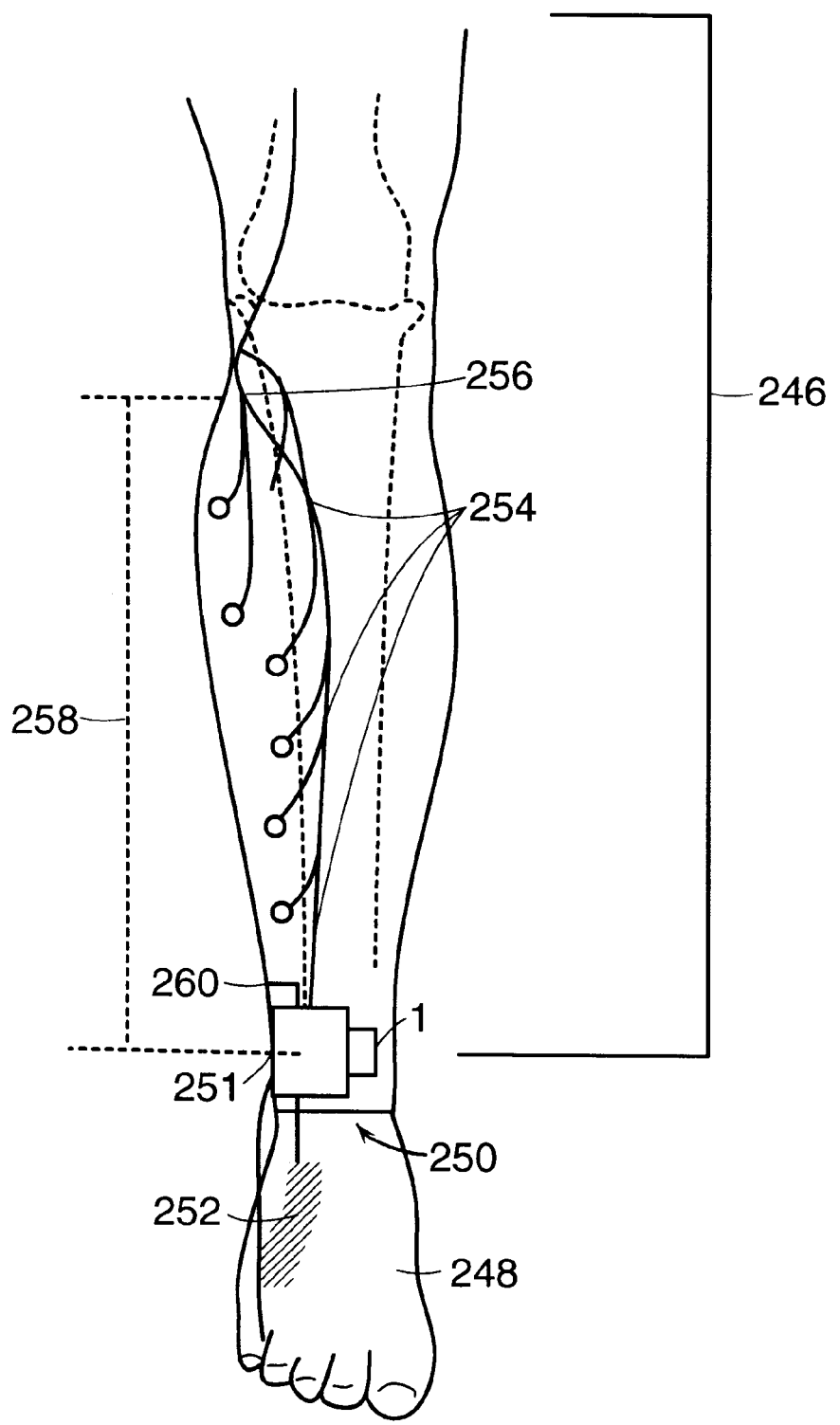
FIG. 1B is an illustration of an embodiment of the apparatus of the invention attached to the ankle joint of a user.

The neuromuscular electrode 1 delivers electrical stimuli to the skin surface, detects biopotentials from the skin surface and measures additional physiological and biological parameters, such as, for example, skin temperature. As shown in FIG. 1A, the neuromuscular electrode 1 is placed on the anterior aspect of the forearm 8 immediately proximal to the wrist crease 9. In another embodiment, as shown in FIG. 1B, the neuromuscular electrode is placed on the lateral anterior surface of the lower leg 246 proximal to the ankle joint 250. In the preferred embodiment, the physical dimensions of the neuromuscular electrode 1 are chosen from a predetermined set of dimensions which are optimized for the range of wrist or ankle joint sizes found in adults. For example, the electrodes may be configured in a small, regular, and large size. In a preferred embodiment, the size of the neuromuscular electrode 1 is chosen according to a size chart, which matches patient characteristics, such as height and weight, to an appropriate size. Additional embodiments are contemplated in which the neuromuscular electrode 1 includes means to vary its physical dimensions over a predetermined range, such as, for example, being contained in an electrode housing, such as, an adjustable band or strap. The band or strap may also be detachable.

Figure 2A:
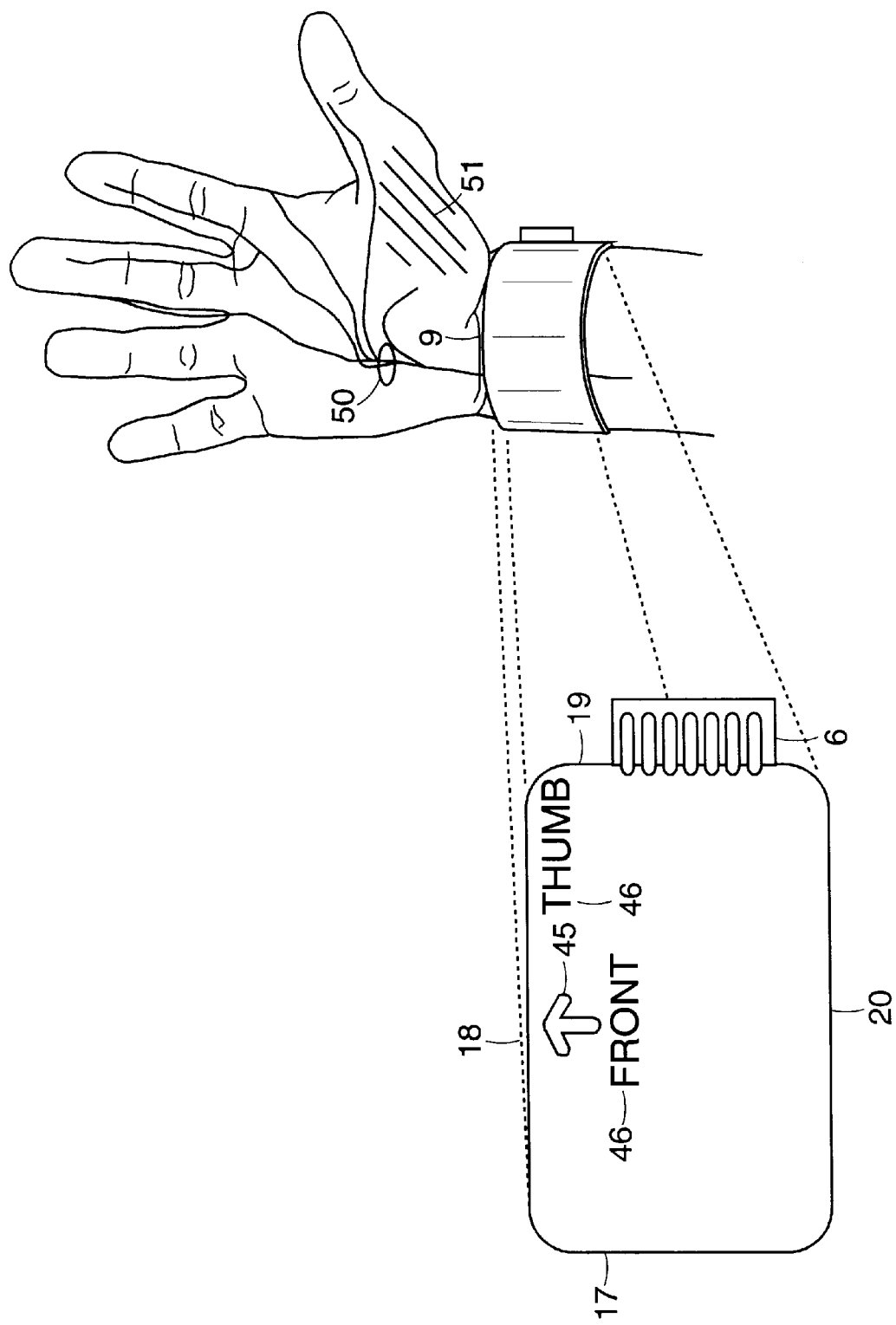
FIG. 2A shows a top surface of the embodiment of the apparatus of the invention shown in FIG. 1A.
Figure 2B:
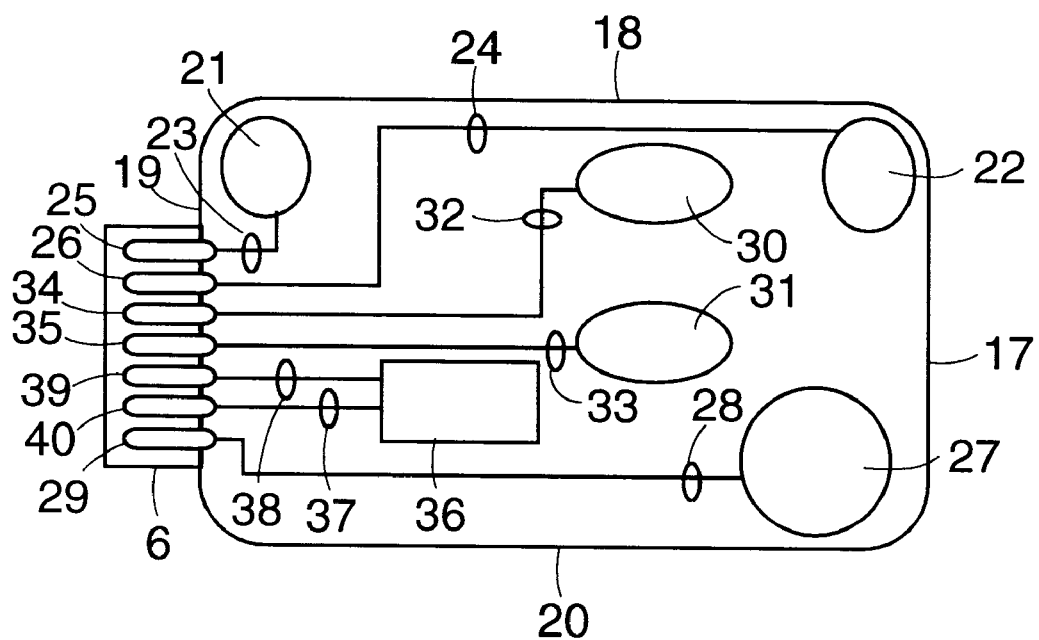
FIG. 2B illustrates a bottom surface of the embodiment of the apparatus of the invention shown in FIG. 1A depicting an electrode configuration.

An illustrative embodiment of the neuromuscular electrode 1 is shown in FIG. 2A. FIG. 2A shows the top surface of the neuromuscular electrode 1 and its proper location on the user's wrist. In one embodiment, the top surface of the neuromuscular electrode 1 contains printed instructions 46 and/or other visual indications 45 to help the user properly position it. FIG. 2B shows the bottom surface of the neuromuscular electrode 1. The illustrative configuration allows muscle activity in the thenar muscle group 51 to be evoked and sensed when the neuromuscular electrode 1 is positioned immediately proximal to the wrist crease 9, as shown in FIG. 2A. Two bioelectrical transduction sites, 30 and 31, hereafter referred to as the stimulation sites, are positioned approximately midway between the lateral end 19 and medial end 17 of the neuromuscular electrode 1. The two stimulation sites, 30 and 31, are arranged in a distal to proximal line such that one of the sites is near the distal end 18 of the neuromuscular electrode 1 and one of the sites is near the proximal end 20 of the neuromuscular electrode 1.

The stimulation sites may consist of stimulation electrodes having delineated areas of bioelectrical signal transduction means that convert electronic signals into electrochemical ones and vice versa. In a preferred embodiment, these sites are composed of a plurality of layers of different materials with substantially the same area. A first layer is directly attached to the bottom face of the neuromuscular electrode 1 and is preferably formed by a thin layer of silver. A second layer is attached to first layer and preferably consists of a silver-chloride salt. A third layer is attached to second layer and contacts the user's skin on its exposed surface. The third layer is preferably composed of an electrolyte hydrogel, such as, for example, sodium chloride.

When the neuromuscular electrode 1 is properly positioned as shown in FIG. 2A, the two stimulation sites, 30 and 31, will overlie the median nerve 50. The nerve 50 is stimulated by passing a low amplitude current (e.g., typically less than 10 milliamps) through the two stimulation sites, 30 and 31. The current is provided by an external source electrically coupled to contacts, 34 and 35, on the external connector 6. The contacts, 34 and 35, and the stimulation sites, 30 and 31, are coupled by electrically conductive and insulated means, 32 and 33.

Two transduction sites, 21 and 22, hereafter referred to as the detection sites, are positioned at the extreme lateral end 19 and medial end 17 of the neuromuscular electrode 1 near its proximal end 18. In a preferred embodiment, the detection sites, 21 and 22, consist of detection electrodes comprised of delineated areas of bioelectrical signal transduction means that convert electronic signals into electrochemical ones and vice versa. In a preferred embodiment, these sites are constructed in a substantially similar manner to the stimulation sites, 30 and 31.

In operation, contraction of the thenar muscles 51, as shown in FIG. 2A, will generate a myoelectric potential and create a bioelectrical potential difference between the lateral 21 and medial 22 detection sites due to the relative proximity of the lateral detection site 21 to the thenar muscles 51. This potential difference may be measured as a small (e.g., typically less than 0.5 mV) differential voltage between contacts, 25 and 26, on the external connector 6. The contacts, 25 and 26, and the detection sites, 21 and 22, are coupled by electrically conductive and insulated means, 23 and 24. The measurement of the differential voltage signal is enhanced by the availability of a reference potential, which is provided by transduction site 27, hereafter referred to as the reference site, or reference electrode. This site is positioned along the medial end 17 of the neuromuscular electrode 1 towards its proximal end 20. The position of the reference site 27 is, however, not critical and has relatively little effect on the function of the invention. In a preferred embodiment, the reference site 27 is constructed in a substantially similar manner to the stimulation sites, 30 and 31, and detection sites, 21 and 22. The reference potential is made available at a contact 29 on the external connector 6, which is coupled to the reference site 27 by electrically conductive and insulated means 28.

In an alternative embodiment, shown in FIG. 1B, the neuromuscular electrode 1 is adapted for placement on the leg 246 of an individual. At this location, the two stimulation sites, 30 and 31, overlie the peroneal nerve 254 and deliver a stimulus to it. Contraction of the extensor digitorum brevis (EDB) muscle 252 of the foot 248, resulting from the stimulation, generates a myoelectric potential between the lateral 21 and medial 22 detection sites due to the differential distance between the detection sites and the EDB muscle 252. It is often advantageous to compare the response of the peroneal nerve 254 evoked by stimulation at multiple sites proximal to the ankle joint 250. Thus, in another embodiment of the invention, the neuromuscular electrode 1 is adapted for stimulation at multiple sites proximal to the ankle joint 250, such as, for example, at the ankle joint 250 and just below the knee 256. In all cases, however, the evoked myoelectric potential is detected by detection electrodes, such as 21 and 22, at or proximal to the ankle joint 250.

The neuromuscular electrode 1 also preferably contains a temperature sensor 36, such as, for example, a DS1820 (Dallas Semiconductor, Dallas, Tex.) or a thermistor. The temperature sensitive part of the sensor 36 contacts the users skin directly or indirectly through an intermediary material that efficiently conducts heat. The temperature sensor 36 can be placed at any available location within the area of the neuromuscular electrode 1. The temperature sensor 36 is powered and transmits temperature information to electronic monitor 2 through two or more contacts, 39 and 40, on the external connector 6. The contacts, 39 and 40, and the temperature sensor 36 are coupled by electrically conductive and insulated means, 37 and 38.

The neuromuscular electrode 1 contains an electrochemical gel that is not intended for multiple applications to a test subject. In particular, once the neuromuscular electrode 1 has been applied to the subject and removed, its operational characteristics may be compromised by the physical distortion and contamination associated with application and removal from the skin. The primary characteristic which may be affected is the critically important electrode-to-skin impedance. Another reason for not reusing the neuromuscular electrode 1 is the potential for spreading infection from one person to another. Thus, it is clearly desirable that the neuromuscular electrode 1 is disposable and non-reusable. Consequently, it is important to ensure that the neuromuscular electrode 1 cannot be reused.

Another embodiment of the invention therefore includes a neuromuscular electrode 1 having a data memory for storing a signal representative of a characteristic of the neuromuscular electrode. In a preferred embodiment, this data memory is integrated into the temperature sensor 36, such as the DS1820 (Dallas Semiconductor, Dallas, Tex.), which contains a universally unique 64 bit number in ROM and several bytes of non-volatile EEPROM. The characteristics of the neuromuscular electrode may include the size of the neuromuscular electrode, the height of the individual associated with the size of the neuromuscular electrode, the serial number of the neuromuscular electrode, an indication that the neuromuscular electrode has been used on an individual, or an indication that the neuromuscular electrode has not been used on an individual.

The serial number is provided by the 64 bit ROM, and the other characteristics of a height or size of the neuromuscular are provided by programming one or more bits of the EEPROM during manufacturing of the neuromuscular electrodes 1. The characteristic of an indication that the neuromuscular electrode has been used on an individual is provided by reading and writing one or more bits of EEPROM during regular use. For example, in a preferred embodiment, two of the bits within the EEPROM are used to encode the size of the neuromuscular electrode 1. In particular, the small size is encoded as 00, the medium size as 01, and the large size as 10. Furthermore, in a preferred embodiment, one of the bits within the EEPROM is used to inactivate the neuromuscular electrode 1 after use. In particular, an activated neuromuscular electrode 1 is encoded as a 0 and an inactivated one is encoded as a 1.

In another embodiment of the neuromuscular electrode 1, the serial number is printed on one or more removable labels attached, for example, to the top surface of the neuromuscular electrode 1.

Additional configurations and arrangements of transduction sites and sensors have been contemplated and should be considered within the scope of the present invention. One such configuration utilizes a single pair of transduction sites for both stimulation and detection through electronic multiplexing.

The electronic monitor 2 has a number of functions. The monitor 2 detects, amplifies, processes and stores bioelectrical potentials, such as those generated by nerve or muscle activity. It also generates stimuli, such as steps of electrical current, with sufficient magnitude to trigger impulses in nerves or muscles. In addition, it communicates with the user and with external instruments, such as, for example, a personal computer. Finally, the electronic monitor 2 includes a controller to process data and control the intensity and duration of stimulus applications.

Figure 3:
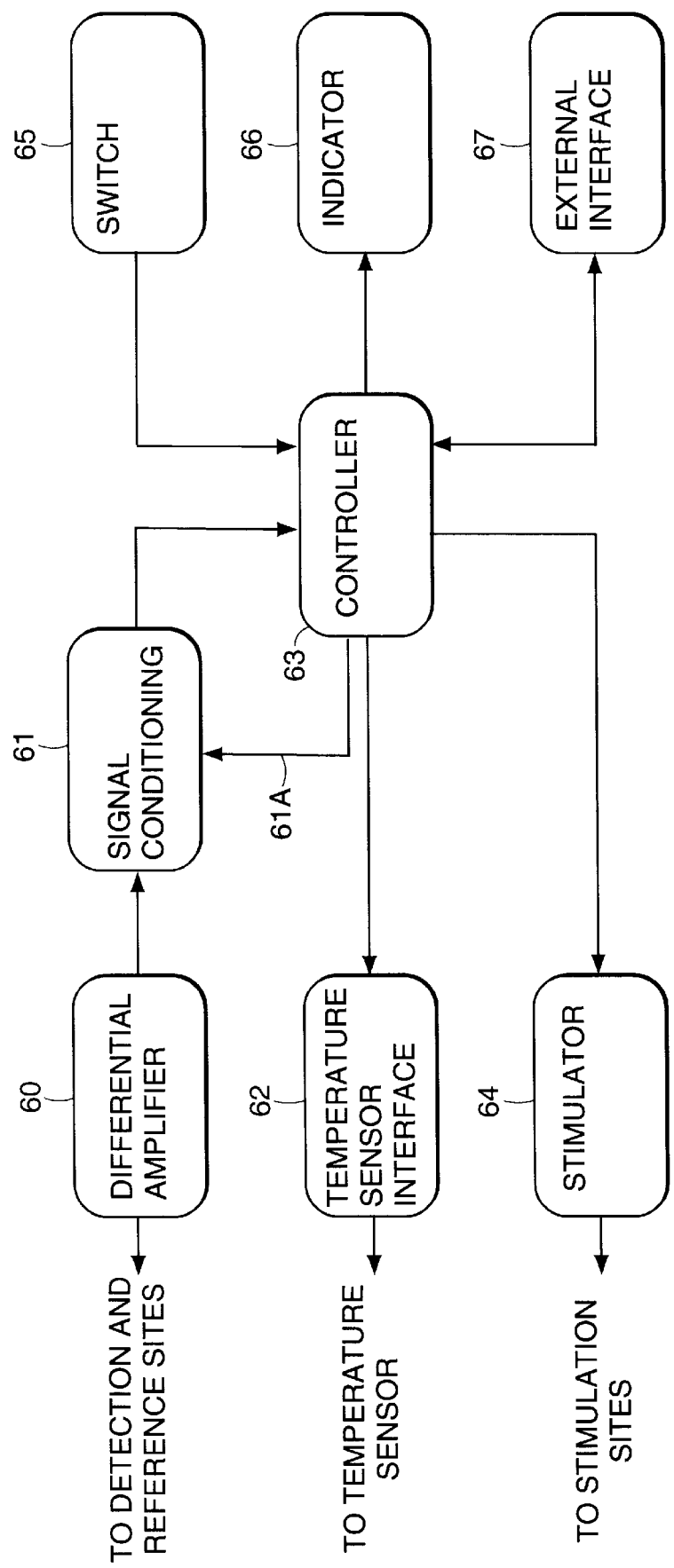
FIG. 3 is a block diagram of an embodiment of the apparatus of the invention.

An illustrative block diagram of the electronic monitor 2 of FIG. 1A is shown in FIG. 3. Differential amplifier 60 amplifies the voltage difference between the input terminals and generates a voltage that is proportional to that voltage difference. When the electronic monitor 2 and neuromuscular electrode 1 of FIG. 1A are connected by physical contact between connectors, 6 and 7, the differential amplifier 60 of FIG. 3 is electrically coupled to detection sites, 21 and 22, and reference site 27. Since the bioelectrical signals from the body surface typically have a source impedance between about 5 K$\Omega$ to about 50 K$\Omega$ and contain large common mode signals, the differential amplifier 60 must have a high input impedance, a good common mode rejection ratio and a low leakage current. These requirements are preferably met by an instrumentation amplifier, such as, for example, the INA111 (Burr-Brown, Tuscon, Ariz.) or the AD621 (Analog Devices, Norwood, Mass.).

The differential amplifier 60 is electrically coupled to a signal conditioning unit 61 that prepares the signal for analog-to-digital conversion and subsequent processing. The signal conditioning unit 61 preferably removes DC offsets, amplifies, low-pass filters, performs variable gain amplification, and creates a DC bias. Variable gain amplification is controlled by controller 63 using gain control line 61A. The output of the signal conditioning unit 61 is electrically coupled to one or more analog-to-digital converters on the controller 63.

Temperature sensor interface electronics 62 power the temperature sensor and convert temperature related signals into a form interpretable by controller 63. Stimulator 64 generates an electrical impulse with either or both of the magnitude and duration of the impulse being determined by signals from controller 63.

The stimulator 64 is preferably embodied by a circuit which gates the discharge of a capacitor charged to a high voltage (e.g., 100 volts). The capacitance value (e.g., 1 $\mu$F is chosen so that the discharge time constant (e.g., several seconds) is much longer than the typical impulse duration (e.g., less than 1 millisecond). The voltage across the capacitor is established by internal charging means, such as, for example, a DC-DC converter. In another embodiment, it is established by external charging means. In the later case, the stimulator 64 is capable of generating a finite number of electrical impulses before it has to be recharged by the external charging means.

Actuating means 65 are electrically coupled to processor 63 and preferably embodied by one or more push button switches. Indicator 66 is also electrically coupled to controller 63 and preferably embodied in a single, or multi-segment, LED. Finally, external interface 67 is electrically coupled to controller 63 and preferably embodied as a standard RS-232 serial interface. The controller 63 performs analog-to-digital conversion, senses and controls I/O lines, and processes, analyzes and stores acquired data. The controller 63 is preferably embodied as a single, integrated, low-cost embedded microcontroller. However, in other embodiments, the controller 63 is configured with multiple components, such as, for example, a microprocessor and external components that perform analog-to-digital conversion and other necessary functions.

Figure 4:
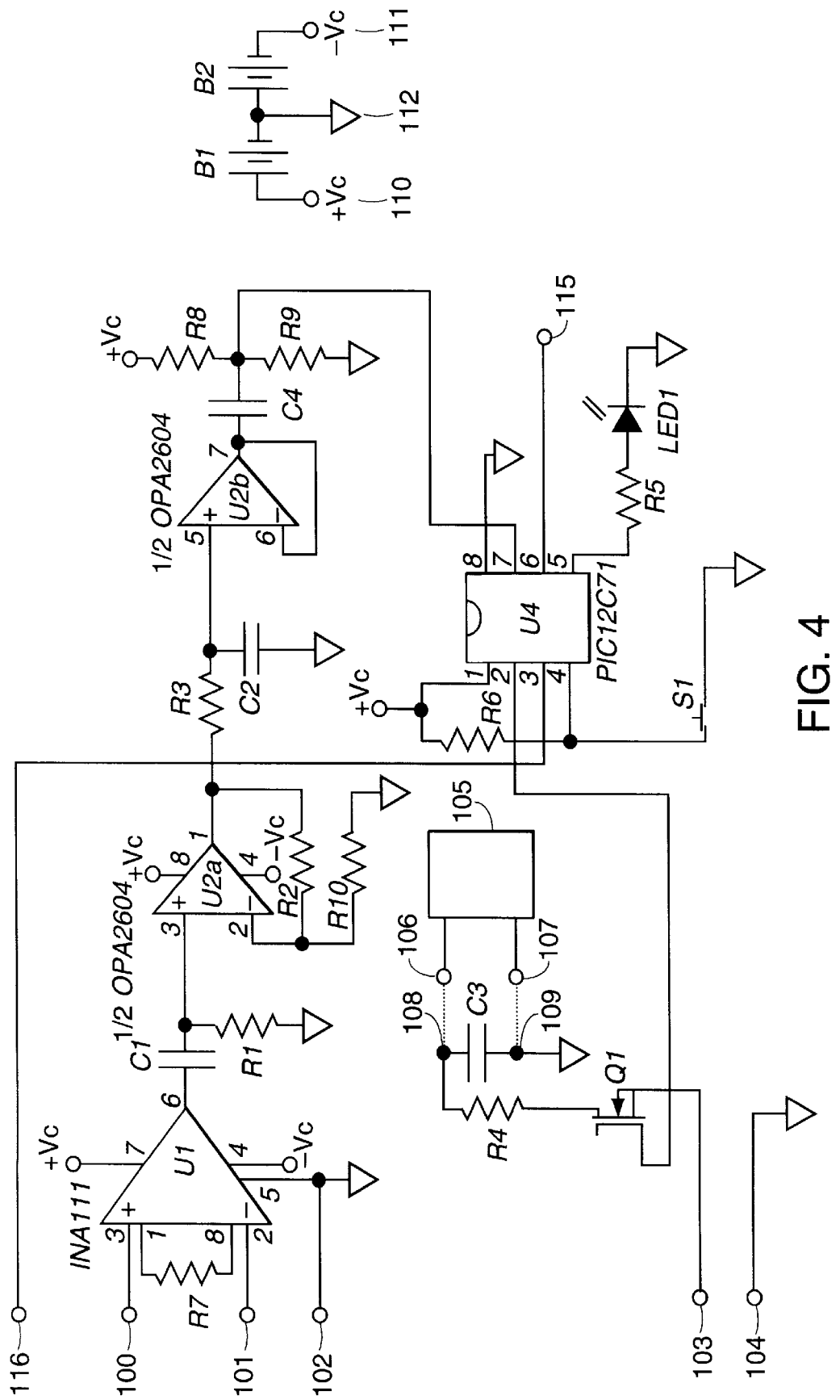
FIG. 4 illustrates electronic circuitry for an embodiment of an apparatus of the invention.

FIG. 4 shows a schematic diagram of the circuitry of one embodiment of the electronic monitor 2 of FIG. 1A. The illustrative circuit of FIG. 4 includes a detection sub-circuit, a stimulation sub-circuit and a control and processing sub-circuit. The detection stage is based on amplifier U1, a type INA111 (Burr-Brown, Tucson, Ariz.) instrumentation amplifier. Each of a pair of inputs of amplifier U1, 100 and 101, is electrically coupled to one of the detector sites, 21 and 22, of FIG. 2B. In addition, amplifier U1 has a reference pin 102 at which it receives a reference potential through electrical coupling to reference site 27 of FIG. 2B. U1 is a monolithic instrumentation amplifier and requires one external component, a resistor, R7, to establish its amplification gain, which is preferably a factor of 10. Amplifier U1 is powered by a two sided symmetrical power supply providing +Vc 110 and −Vc 111 (e.g., 6 volts), as well as a ground 112. In a preferred embodiment, +Vc 110, −Vc 111, and the ground 112 are provided by two batteries, B1 and B2, connected in series, as shown in FIG. 4. The output of amplifier U1 is coupled through a high pass filter formed by capacitor C1 and resistor R1 to the input of a non-inverting amplifier formed by operational amplifier U2a. The high pass filter removes any DC offset in the output of amplifier U1.

In a preferred embodiment, capacitor C1 and resistor R1 are chosen for a high pass corner frequency of about 2 Hz. The gain of the non-inverting amplifier is established by resistors R2 and R10 and is preferably set to a gain of 500. The gain of U2a can be made variable by converting R2, R10, or both R2 and R10 into digital potentiometers under the control of microcontroller U4. The output of first operational amplifier U2a is coupled to input of second operational amplifier U2b by a low pass filter formed by resistor R3 and capacitor C2. The low pass filter removes high frequency noise from the signal. In a preferred embodiment, resistor R3 and capacitor C2 are chosen for a low pass corner frequency of about 3 KHz. The second operational amplifier U2b is configured simply as an impedance buffer. The output of amplifier U2b is coupled to an analog-to-digital conversion pin on microcontroller U4 by a DC biasing circuit consisting of capacitor C4, along with resistors R8 and R9. The purpose of the DC biasing circuit is to insure that all signals vary from ground 112 to +Vc 110, since the analog-to-digital conversion electronics of microcontroller U4 operate only on positive voltages. The detection stage also has a combination communication and power line 116, for interfacing to a "one-wire" temperature sensor 36 of FIG. 2B, connected to an I/O pin on microcontroller U4.

The stimulation sub-circuit of the apparatus is based on energy storage capacitor C3, which is a high capacitance (e.g., 1 $\mu$F or greater) and high voltage (e.g., greater than 1100 volts) capacitor. In one embodiment of the apparatus, capacitor C3 is charged to greater than 100 volts by an external charging means 105. Capacitor C3 charging is accomplished by charging means 105, which passes electrical current between terminals 107 and 106, which are temporarily electrically coupled to capacitor C3 terminals 109 and 108 during the charging period. Once capacitor C3 is charged, charging means 105 is removed. Electrical stimulation of nerve and muscle is accomplished by discharging capacitor C3 through leads 103 and 104, which are electrically coupled to stimulation sites, 30 and 31. Control of stimulation duration is provided by a power MOSFET transistor Q1, which gates discharge according to a digital signal from microcontroller U4. Resistor R4 protects transistor Q1 by limiting the current that flows through it.

The control and processing stages of the apparatus are based on microcontroller U4, which is preferably a type PIC12C71 (MicroChip, Chandler, Ariz.) microcontroller. U4 provides processing and storage capabilities, analog-to-digital conversion and input/output control. In addition to the aforementioned connections to detection and stimulation subcircuits, microcontroller U4 detects depression of switch S1, which is connected to an I/O pin and controls light emitting diode LED1, which is also connected to an I/O pin. Resistor R6 limits current into the I/O pin when switch S1 is depressed and resistor R5 limits current through the light-emitting diode LED1. In addition, serial communication 115 to external devices is provided by the remaining available I/O pin. Control and processing algorithms are stored in microcontroller U4 and executed automatically upon application of power. Other electronic circuitry may be used to perform the processes described above and is considered to be within the scope of the invention. One skilled in the art knows how to design electronic circuitry to perform the functions outlined above.

Figure 5:
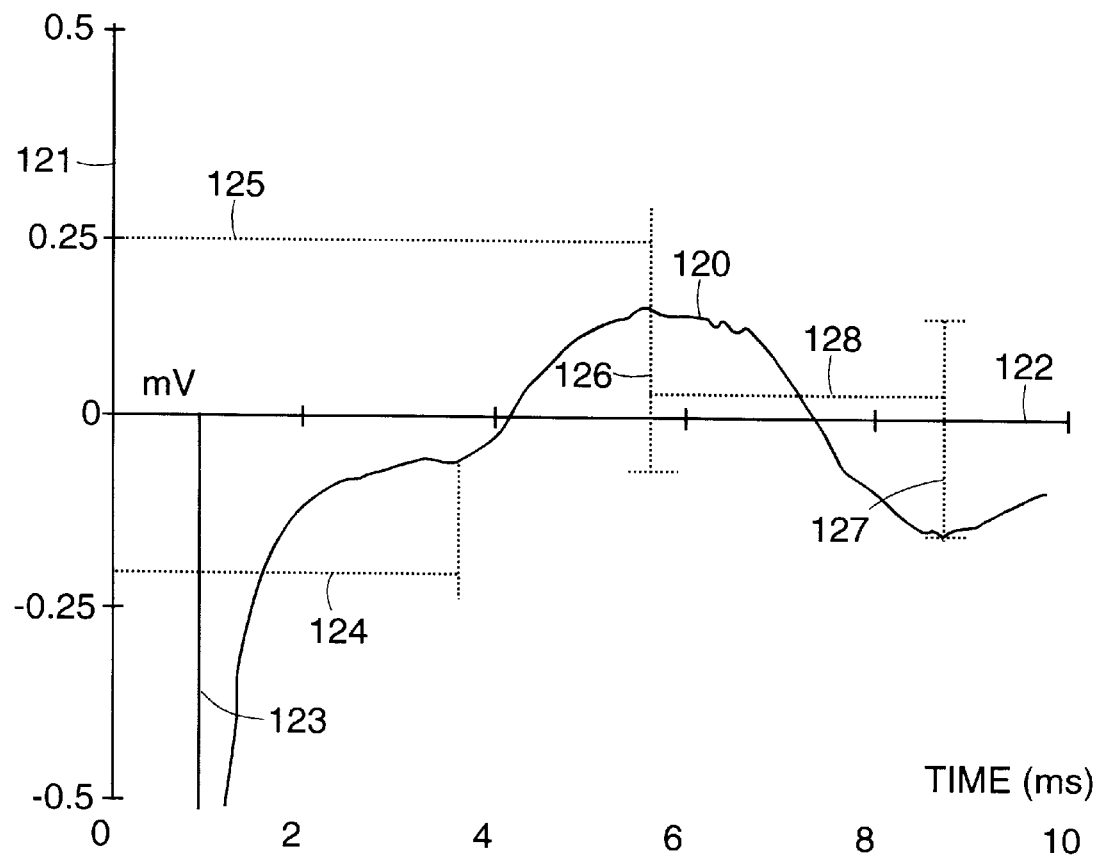
FIG. 5 is a graph showing a M-wave muscle response evoked and measured by an apparatus of the invention.

A major object of the present invention is to serve as a detection system for CTS. Conventional detection of CTS is based on an analysis of certain features of the evoked M-wave muscle response, typically the distal motor latency (DML). Referring to FIG. 1A, the DML represents the time lag between stimulation of the median nerve 50 immediately proximal to the wrist crease 9 and arrival of the neurally conducted impulse at the thenar muscle group 51 after direct orthodromic conduction through the wrist (i.e., after traversing the Carpal Tunnel). Thus, the DML quantifies nerve conduction in the distal most segment of the median nerve. One of the most common and consistent indications of CTS is an increase in the DML. Although there is no single definition for the DML, it is generally defined as the amount of time that elapses between the start of the stimulus (i.e., time=0) and the occurrence of a consistent feature on the muscle response. A typical M-wave muscle response 120, evoked and acquired using an apparatus of the invention, is shown in FIG. 5. The vertical scale 121 indicates the amplitude of the muscle response in millivolts as measured between detection sites 21 and 22. The horizontal scale 122 indicates the elapsed time from the onset of the stimulation pulse (i.e., stimulus occurred at time=0). The large signal transients 123 that occur in the first 2 milliseconds represent stimulus associated artifacts and are unrelated to activity in the thenar muscles 51. An evoked muscle response 120 may be characterized by many parameters including, but not limited to, a time to onset 124, a time to peak 125, a peak amplitude 126, a peak to peak amplitude 127 and a peak to peak width 128. In the illustrative example of FIG. 5, the time to onset 124 is about 3.7 milliseconds, and the time to peak 125 is about 5.8 milliseconds.

Because detection of the thenar muscle 51 response occurs at a significant distance from its physiological site of origin, the intervening tissue acts as a low pass filter. This results in amplitude attenuation and temporal spreading of the detected waveform as compared to measurements taken directly over the thenar muscles 51. The decrease in amplitude results in a reduction in the signal-to-noise ratio of the detected M-wave 120 response. The temporal spreading obscures sharp characteristic features of the M-wave response 120. Taken together these two low-pass related effects make a consistent and accurate identification of muscle response features, such as the time to onset 124 or the time to peak 125, difficult and highly variable, especially in the presence of various noise sources (e.g., extraneous muscle activity such as would be caused by a muscle twitch in an arm muscle).

In a preferred embodiment, analysis of the M-wave muscle response 120 is significantly enhanced by preprocessing it prior to determination of its characteristic features. One such preprocessing step is to take the second derivative of the M-wave muscle response 120 as shown in FIG. 6A. The advantageous nature of this preprocessing step is evident from the fact that the second derivative 130 (solid line) has a peak 131 near the onset 124 of the M-wave muscle response 120. Consequently, it is possible to accurately and consistently obtain a latency estimate 133 by simply detecting the presence of this peak 131. By contrast, a direct estimation of the time to onset 124 from the M-wave muscle response 120 requires establishment of an arbitrary voltage threshold which may vary significantly among different individuals.

Figure 6:
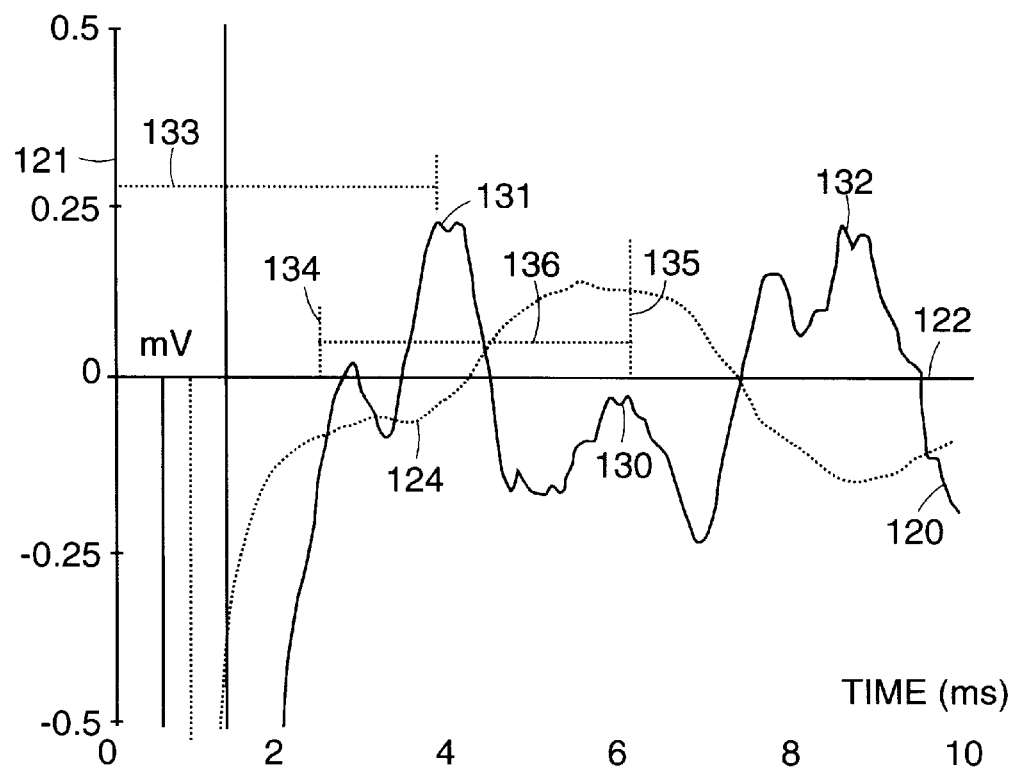
FIG. 6 is a graph showing a second derivative of a M-wave muscle response signal evoked and measured by an apparatus of the invention.

In a preferred embodiment, the sharp peak 131 in the second derivative 130 of FIG. 6 is obtained by first smoothing the muscle response 120, such as by, for example, convolving it with a normalized Gaussian waveform with a predetermined standard deviation. Subsequently, the first derivative is calculated by estimating the instantaneous slope for each data point in the muscle response 120. The second derivative is then calculated by estimating the instantaneous slope for each data point in the just computed first derivative. In order to conserve dynamic memory resources, the first and second derivatives 130 can be sequentially calculated for small sections of the muscle response 120 and the values discarded if they do not indicate the presence of a peak 131 in the second derivative 130.

Once the peaks 131 in the second derivative 130 have been identified, the largest positive peak within a defined time window 136 is selected. This time window 136 is defined as occurring between two time limits, 134 and 135. In a preferred embodiment, the lower time limit 134 is predetermined and reflects the amount of time required for artifacts 123 associated with the stimulus to decay to an amplitude that is significantly less than the amplitude of the actual signal evoked from the muscle 120. The lower time limit 134 is preferably about 2.5 milliseconds. Other lower time limits may, however, be used. In addition, it is possible to dynamically establish the lower time limit 134 by analyzing the amplitude decay of the stimulus associated artifact 123. The upper time limit 135 is determined dynamically. In a preferred embodiment, the upper time limit 135 is set to reflect the time during which the first derivative of the evoked muscle response 120 is positive. In other words, it reflects the period of time during which the evoked muscle response 120 is increasing. By establishing the upper time limit 135 in this fashion, large peaks 132 in the second derivative of the response 130, which occur in the latter portion of the response, are ignored and, therefore, do not result in incorrect estimates of the latency 133.

Figure 7:
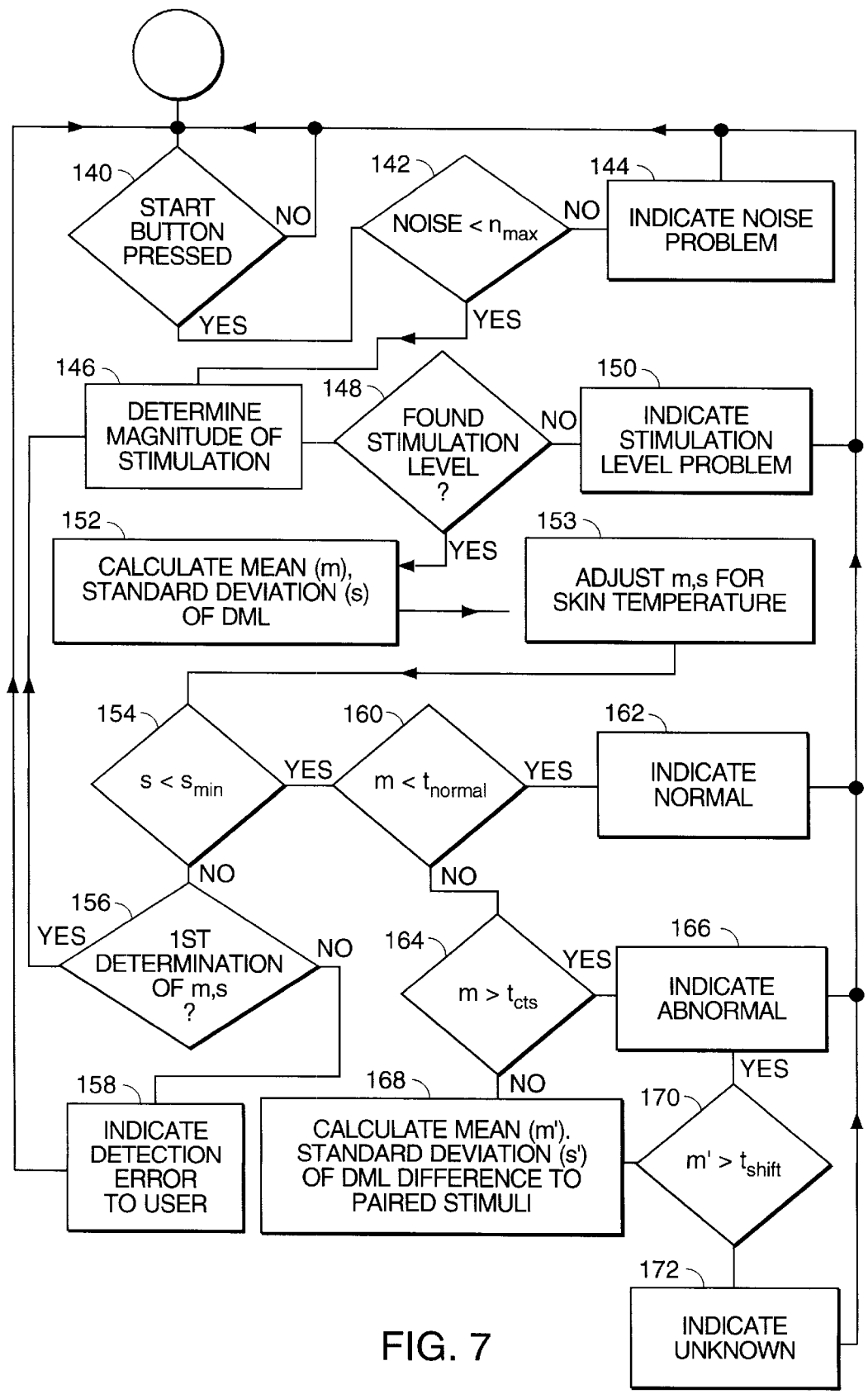
FIG. 7 is flow chart of an embodiment of an algorithm for detecting carpal tunnel syndrome using an apparatus of the invention.

In accordance with a preferred embodiment of the present invention, FIG. 7 shows an illustrative algorithm for detecting CTS using an apparatus of the invention in an entirely automated fashion. The algorithm commences in process step 140 by activation of actuating means 65, such as, for example, by depression of a START switch S1. If the actuation means have been activated, the algorithm continues with process step 142. Otherwise process step 140 is continuously executed until the actuating means are activated. In process step 142, the root-mean-square (RMS) value of the noise is obtained in the absence of any electrical stimulation and compared against a predetermined threshold, $n_{max}$. If the noise RMS is less than $n_{max}$, the algorithm continues with process step 146. However, if the noise RMS is greater than $n_{max}$, the algorithm proceeds to process step 144, in which indicator 66 is used to indicate a problem with the noise level to the user. Subsequently, the algorithm returns to process step 140 and waits for reactivation of the START switch S1.

In process step 146, the magnitude of stimuli to be used in diagnosing CTS is determined. In a preferred process, this parameter is determined automatically without user involvement. This is accomplished by gradually increasing the stimulation duration in predetermined increments (e.g., 25 microseconds) until the evoked muscle response 120 meets one or more predetermined criteria. As an illustrative example, the stimulation duration is increased until the peak of the first derivative of the evoked muscle response 120 exceeds a predetermined threshold (e.g., 0.1 mV/ms). If the proper stimulation duration is obtained, the algorithm proceeds from process step 148 to process step 152. If a proper stimulation magnitude is not obtained, (ie., predetermined threshold not exceeded) the algorithm proceeds to process step 150, in which indicator 66 is used to indicate a problem with the determination of stimulation magnitude to the user. Subsequently, the algorithm returns to process step 140 and waits for reactivation of the START switch.

Upon determination of the proper stimulation magnitude, the algorithm proceeds with process step 152. In this step, the median nerve 50 is stimulated at a predetermined rate (e.g., 2 Hz) for a predetermined duration (e.g., 2 seconds). Each thenar muscle response 120 is analyzed, as previously described, to estimate the distal motor latency (DML) as the first major peak 133 of the second derivative 130 of the muscle response 120. Furthermore, the plurality of DML estimates are combined to obtain a mean DML (m) and a standard deviation (s) about this mean. The algorithm then proceeds to process step 153 in which m and s are adjusted for variations in skin temperature. In particular, the following two adjustment equations are applied:

$$m_{corrected} = m_{uncorrected} + k_1 T + k_2 \qquad (A)$$

$$s_{corrected} = s_{uncorrected} + k_1 T + k_2 \qquad (B)$$

The corrected mean DML ($m_{corrected}$) and standard deviation ($s_{corrected}$) represent the expected values at room temperature (i.e., 25° C. or 298° K.). The skin temperature, as measured by the temperature sensor 36, is represented by the variable T. The values of constants $k_1$ and $k_2$ are determined by a temperature calibration process. In this process, multiple measurements of the mean DML are obtained at a variety of temperatures spanning the expected range of temperatures over which the invention is normally used (e.g., 25° C. to 40° C.). Subsequently, a linear regression is performed between the temperatures and the mean DML measurements. The constants $k_1$ and $k_2$ are determined directly from the regression coefficients.

The algorithm then continues with process step 154, in which the standard deviation of the DML measurements, s, is compared against a predetermined threshold, $s_{min}$. If s is larger or equal to $s_{min}$, process step 156 is executed. Process step 156 evaluates the number of times m and s have been determined. If these values have been calculated only once, the algorithm returns to process step 146, where determination of the proper stimulation level and all subsequent processing is repeated. If m and s have been determined twice, however, process step 158 is executed, resulting in indication of a diagnostic error to the user through indicator 66. Subsequently, the algorithm returns to process step 140 and waits for reactivation of the START switch S1.

If in process step 154 it is determined that s is less than $s_{min}$, the algorithm proceeds with process step 160. In this step, the mean of the DML estimates, m, is compared against a first predetermined latency threshold, $t_{normal}$. If m is less than $t_{normal}$, the algorithm proceeds to process step 162, in which a normal (i.e., user does not have CTS) test result is indicated to user through indicator 66. Subsequently, the algorithm returns to process step 140 and waits for reactivation of the START switch S1. If m is greater or equal to $t_{normal}$, the algorithm proceeds with process step 164, in which the mean distal motor latency, m, is compared against a second predetermined latency value, $t_{CTS}$. If m is greater than $t_{CTS}$, the algorithm proceeds to process step 166, in which an abnormal (i.e., user has CTS) test result is indicated to user through indicator 66. Subsequently, the algorithm returns to process step 140 and waits for reactivation of the START switch S1.

If neither of the two previous inequalities is true, the algorithm continues with process step 168. In this step, the median nerve 150 is stimulated by pairs of electrical stimuli spaced apart at a predetermined temporal interval (e.g., 3 milliseconds). For each evoked muscle response 120, the difference between the DML estimated from the first and second stimuli is determined. Furthermore, the plurality of DML difference estimates are combined to obtain a mean DML difference (m') and a standard deviation (s') about this mean. Upon measurement of these two parameters, the algorithm proceeds to process step 170 in which the mean DML difference, m' is compared against a predetermined threshold, $t_{shift}$. If m' is greater than $t_{shift}$, process step 166 is executed, in which an abnormal test result is indicated to the user, as described above. If this inequality does not hold, then an unknown test result is indicated to user in process step 172. Subsequently, the algorithm returns to process step 140 and waits for activation of the START switch S1.

Another object of the present invention is to serve as a detection system for diabetic neuropathy. Conventional detection of diabetic neuropathy is based on an analysis of certain features of the evoked muscle response, such as the distal motor latency (DML) and the motor nerve conduction velocity (MNCV). Referring to FIG. 1B, the peroneal nerve DML represents the time lag between stimulation of the peroneal nerve 254 proximal to the ankle joint 250 and arrival of the neurally conducted impulse at the EDB muscle 252. The peroneal nerve MNCV is calculated by dividing the distance 258 between two stimulation points proximal to the ankle joint, such as 251 and 256, by the difference between the time lag evoked by stimulation of the peroneal nerve 254 at the first location 251, and the time lag evoked by stimulation of the peroneal nerve 254 at the second location 256. One of the most common and consistent indications of diabetic neuropathy is an increase in the peroneal nerve DML and/or a decrease in the peroneal nerve MNCV. Methods similar to those described above may be used to detect delays and conduction velocities associated with stimulation and detection proximal to the ankle joint 250.

Another major object of the present invention is to detect systemic neuropathies by determining an F-wave latency of a muscle response. The F-wave latency is typically defined as the median interval between the time of administering a stimulus to a motor nerve (i.e., time=0) and the onset of a myoelectric response in a muscle innervated by the nerve following antidromic activation of motor neurons in the spinal cord. Referring again to FIG. 1A, the F-wave latency represents the time lag between stimulation of the median nerve 50 immediately proximal to the wrist crease 9 and arrival of the neurally conducted impulse at the thenar muscle group 51 after antidromic propagation of the impulse to the spinal cord, reflection of the impulse in the anterior horn cells of the spinal cord, and then orthodromic conduction back down the median nerve. Thus, the F-wave latency quantifies nerve conduction over the entire course of the median nerve and includes the brachial plexus and the spinal cord.

It is important to note that, by electrodiagnostic convention, negative deflections are plotted above the horizontal axis and positive deflections are plotted below the horizontal axis. An F-wave latency is generally defined as the amount of time that elapses between the start of the stimulus (i.e., time=0) and the initial positive or negative deflection of the F-wave component.

Figure 8A:
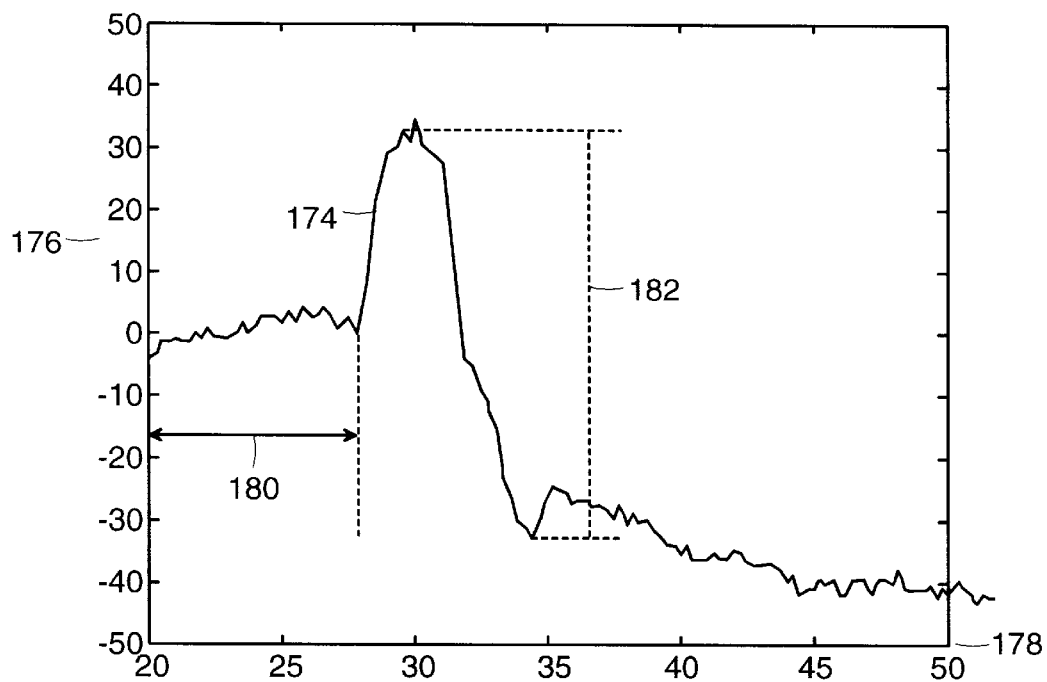
FIG. 8A is a graph showing a F-wave muscle response evoked and measured by an apparatus of the invention.

A typical F-wave muscle response 174, evoked and acquired using an apparatus of the invention, is shown in FIG. 8A. The vertical scale 176 indicates the amplitude of the response in microvolts as measured between detection sites 21 and 22. The horizontal scale 178 indicates the elapsed time from onset of the stimulus pulse (i.e., stimulus occurred at time=0). The F-wave response is primarily characterized by the time to initial deflection 180. However, the peak-to-peak amplitude 182 is occasionally used as well. In the illustrative example of FIG. 8A, the time to initial deflection 180 is 28 milliseconds, and the peak-to-peak amplitude 182 is about 60 microvolts.

Referring again to FIG. 8A, a F-wave response 174 is analyzed to yield the time to the initial deflection 180, typically referred to as the F-wave latency. F-wave latencies may be determined either by stimulation and detection proximal to the wrist or by stimulation and detection proximal to the ankle joint. These F-wave latencies are then correlated to the presence or absence of CTS or to the presence or absence of diabetic neuropathy, respectively.

A F-wave latency is determined first by detecting an F-wave response signal, which is a component of the myoelectric potential. This F-wave response signal is then analyzed to determine the F-wave latency. The analysis includes the steps of removing a trend from the baseline of the myoelectric potential, filtering the myoelectric potential, determining a maximum peak of the F-wave response signal, identifying a first minimum peak and second minimum peak adjacent the maximum peak of the F-wave response signal, determining the amplitude between the maximum peak of the F-wave response signal and one of the two minimum peaks of the F-wave response signal, determining a noise dependent threshold, and comparing this noise dependent threshold to the amplitude between the maximum peak of the F-wave response signal and one of the two minimum peaks of the F-wave response signal. If this amplitude is greater than or equal to the noise dependent threshold, a F-wave latency is determined.

The myoelectric potential and the F-wave response signal 174 are generally contaminated by a significant trend in the baseline. This occurs because the F-wave response 174 is acquired at high gain and is often superimposed on the tail end of the M-wave response 120. Analysis of the F-wave response signal 174 is significantly improved by first removing this trend, as described above. In a preferred embodiment of the algorithm, detrending is performed by determining the best straight-line fit from the myoelectric potential and subtracting that line from the myoelectric potential. In another embodiment, this trend is removed by averaging a plurality of myoelectric potentials and subtracting that average from the individual myoelectric potentials. In yet another embodiment, the statistical distributions of first, and possibly higher, derivatives of each of the plurality of myoelectric potentials are determined. Those signals with regions that are removed by a predetermined factor, such as about 2.5 to about 4.0 standard deviations, from the distribution's mean or other statistical center, are not included for the purposes of averaging, as described above.

The myoelectric potential and F-wave response signal 174 are also contaminated by low and high frequency noise, which makes identification of the onset 180 difficult. The myoelectric potential is, therefore, digitally filtered using a predetermined filter. One filter that may be used is a wiener filter, a type of optimal filter well known to those skilled in the art. The wiener filter for use in an embodiment of the invention identifies a first group of signals that clearly contain F-waves (based on the expertise of a neurophysiologist) and a second group of signals that clearly do not contain F-waves (again, based on the expertise of a neurophysiologist). In an alternative embodiment, the myoelectric potential is filtered by wavelet analysis. Wavelet de-noising is a method of removing noise known to those skilled in the art.

Figure 8B:
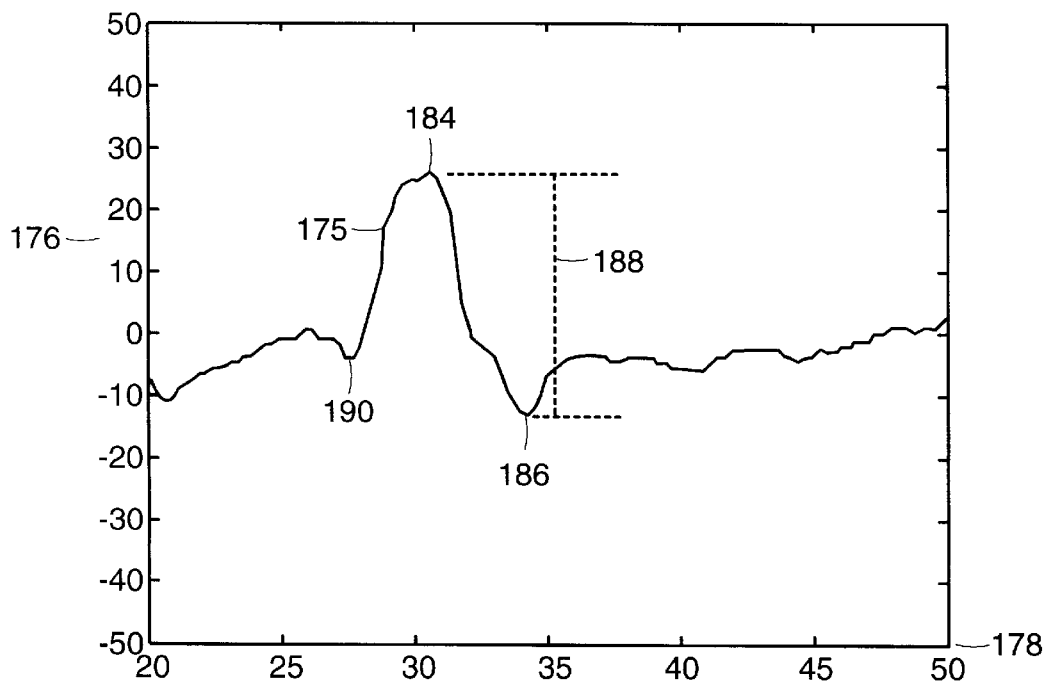
FIG. 8B is a graph showing a digitally filtered F-wave muscle response signal evoked and measured by an apparatus of the invention.

The filtered (and detrended) version 175 of the F-wave response signal 174 is shown in FIG. 8B. All of the local maxima 184 and local minima 186 and 190 of the detrended and filtered myoelectric potential and F-wave response signal 175 are automatically identified. These extrema are preferably determined by identifying those portions of the myoelectric potential for which the first derivative is equal to zero.

The maximum peak 184 of the F-wave response signal and the larger of the two minimum peaks 186 immediately adjacent (e.g., either preceding or succeeding) this maximum peak 184 are then identified. The temporal location and values of these peaks serve as points of reference for deciding whether an F-wave actually exists in the signal and, if so, to determine the F-wave latency 180. In one embodiment, the minimum peak 186 must represent positivity in the signal. In another embodiment, the minimum peak 186 is initially chosen such that it represents positivity in the signal, but if an F-wave is not detected according to these reference points, minima corresponding to negativity in the signal are chosen.

To determine whether a viable F-wave response signal exists in the evoked myoelectric potential, the amplitude 188 between the maximum peak of the F-wave response signal and one of the two minimum peaks of the F-wave response signal, is compared against a noise dependent threshold. The noise dependent threshold is calculated by measuring a level of noise inmmediately preceding or following the acquisition of the myoelectric potential and then multiplying this level of noise by a predetermined factor. The predetermined factor is preferably about 3.5 to about 6.0, but other values are possible. The amplitude 188 is compared against this noise dependent threshold. If the amplitude 188 is greater than or equal to the noise dependent threshold, a F-wave latency exists. If the amplitude 188 is less than the noise dependent threshold, a F-wave latency cannot be reliably determined.

Unlike M-wave 120 of FIG. 5, F-wave 174 can have a multitude of waveform shapes, although most will look similar to the waveform 174 shown in FIG. 8A. Thus, to increase the sensitivity of the determination of a F-wave latency, a number of atypical waveform shapes that do not yield the maximum and minimum peaks of the F-wave response signal, as described above, are detected and processed. For example, in the preferred embodiment, it is recognized that F-wave response signals occasionally have double peaks, such as 196 shown in FIG. 8C. In this situation, the maximum peak 198, may not represent an optimal reference point for determining the F-wave latency 180 (see below for F-wave latency determination). Thus, another local maximum 200 is chosen as a reference point for purposes of latency determination in order to account for this particular waveform irregularity.

In another embodiment, the reference point can be further altered through detection of a minimum peak that is significant in magnitude. This minimum peak preceeds the current reference point (i.e., the maximum peak). In such an instance, the signal would be inverted and the current reference point for the determination of the F-wave latency would be reassigned to the temporal location of this detected minimum peak.

Figure 8C:
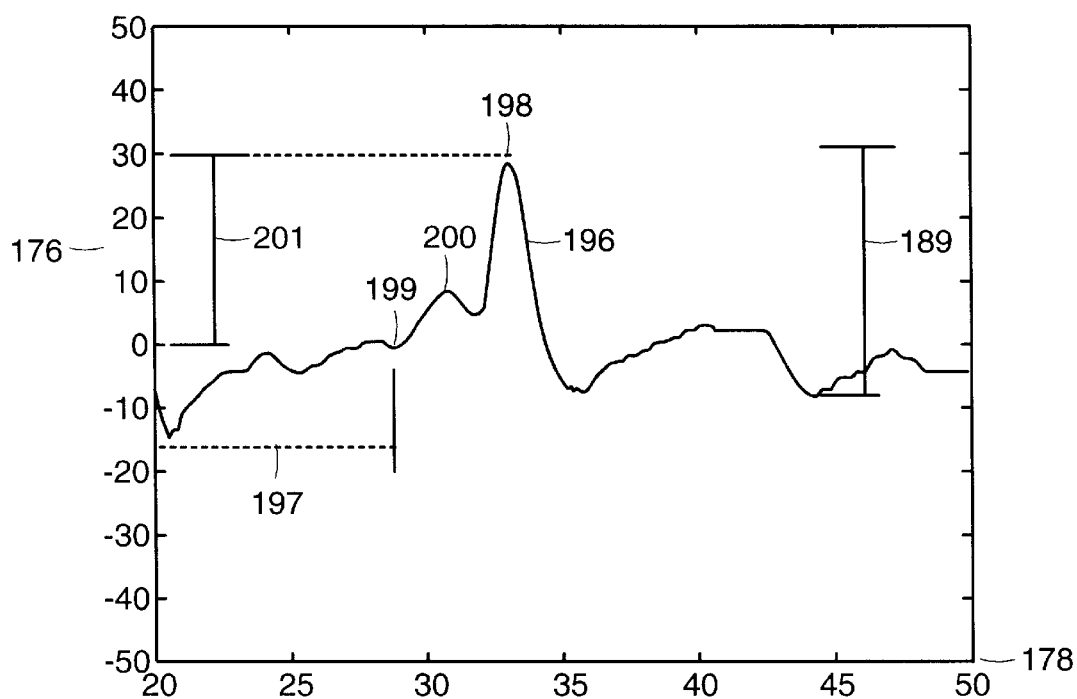
FIG. 8C is a graph showing a F-wave muscle response with double peaks as evoked and measured by an apparatus of the invention.

Referring to FIG. 8C, the F-wave latency 197 of the evoked response is determined when the amplitude 189 is greater than or equal to the noise dependent threshold, as described above. The F-wave latency 196 is identified by determining an inflection 199 in the F-wave response signal immediately preceding the reference point 200 in the F-wave response signal. In an embodiment of the invention, this inflection is identified as the last point preceding the minimum peak of the F-wave response signal for which the signal's first derivative is 0 or negative. If no such point exists, the inflection can be identified as the last point at which the first derivative is at its minimum.

After the F-wave latency is determined, the signal is reanalyzed to confirm the F-wave latency by ensuring that the F-wave latency makes sense within the context of the entire signal. In one embodiment, this is accomplished by, for example, averaging the absolute values of the F-wave response signal in a first predetermined window of time preceeding the F-wave latency 197 and comparing this value to the absolute value of the maximum and minimum first derivative of the F-wave response signal 196 in a second predetermined window of time following the F-wave latency 197. Another method of confirming the F-wave latency includes determining that there are no positive or negative extrema preceding the F-wave latency point 197 that are significant (i.e., greater than 50%, but preferably in the range of about 25% to about 75%) in magnitude with respect to the amplitude of the maximum peak of the F-wave response signal 201. If either of the two confirmation determinations described above fail, an F-wave latency is not yielded.

Once a F-wave latency is determined, this F-wave latency is correlated to an indicia of the latency. This indicia is indicated, but may also be correlated to a physiological function of the nerve and/or muscle. The physiological function may relate to a disorder of a peripheral nervous system of the test subject, such as CTS or diabetic neuropathy. Furthermore, F-wave latencies so determined may be modified in response to the temperature of skin at the test site, in response to the height of the test subject, or in response to the age of the test subject, all as described below.

Figure 9:
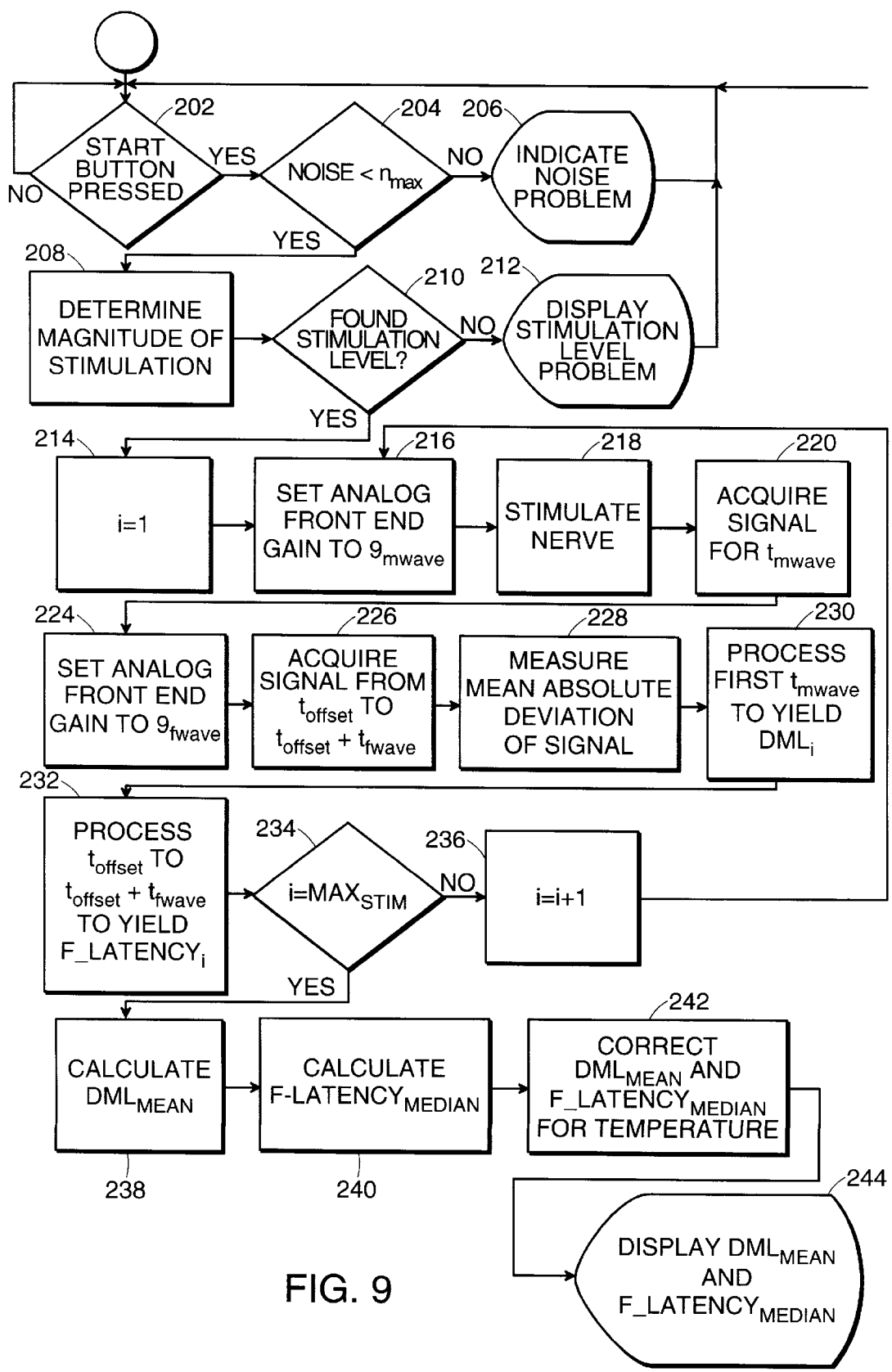
FIG. 9 is a flow chart of an embodiment of an algorithm for detecting a F-wave latency using an apparatus of the invention.

In accordance with a preferred embodiment of the present invention, FIG. 9 shows an illustrative algorithm for measuring the DML and F-wave latency of a peripheral nerve using an apparatus of the invention in an entirely automated fashion. The algorithm commences in process step 202 by activation of actuating means 65, such as, for example, by depression of the START switch S1. If the actuation means have been activated, the algorithm continues with process step 204. Otherwise process step 202 is continuously executed until the actuating means are activated. In process step 204, the mean absolute deviation of the noise is obtained in the absence of any electrical stimulation and compared against a predetermined threshold, $n_{max}$. If the mean absolute deviation of the noise is less than or equal to $n_{max}$, the algorithm continues with process step 208. If the mean absolute deviation of the noise is greater than $n_{max}$, the algorithm proceeds to process step 206, in which indicator 66 indicates to the user a problem with the noise level. Subsequently, the algorithm returns to process step 202 and waits for reactivation of the START switch S1.

The mean absolute deviation of the noise, $\phi$, is calculated according to the following equation:

$$\varphi = \frac{1}{N}\sum_{i=0}^{N}|\bar{n} - n_i| \text{ where } \bar{n} = \frac{1}{N}\sum_{1}^{N}n_i$$

The individual noise samples, $n_i$, are acquired by the controller 61 at a predetermined sampling frequency for a predetermined duration of time. The sampling frequency is chosen so that consecutive samples are unlikely to be correlated and is between about 100 Hz and about 1000 Hz, and is preferably about 500 Hz. The sampling duration is chosen so that a stable measurement of the noise is obtained, and is between about 100 milliseconds and about 1000 milliseconds, and preferably about 200 milliseconds. The mean absolute deviation of the noise is functionally similar to the standard deviation or root mean square of the noise, but, because it does not involve squaring and square-root operations, the mean absolute deviation of the noise is more readily implemented in an efficient manner in a microcontroller. The predetermined noise threshold, $n_{max}$, is generally in the range of about 1 $\mu$V to about 15 $\mu$V, and is more preferably in the range of about 1 $\mu$V to about 5 $\mu$V.

In process step 208, the magnitude of the stimuli used in measuring the DML and F-wave latency is determined. In a preferred process, this parameter is determined automatically without user involvement. If the proper stimulation duration is obtained, the algorithm proceeds from process step 210 to process step 214. If a proper stimulation magnitude is not obtained, the algorithm proceeds to process step 212, in which indicator 66 indicates to the user a problem with the determination of stimulation magnitude. Subsequently, the algorithm returns to process step 204 and waits for reactivation of the START switch.

Upon determination of the proper stimulation magnitude, the algorithm proceeds with process step 214. In this step, a stimulation counter, i, is initialized to a value of one. The algorithm then proceeds to process step 216 in which the gain of the signal conditioning subsystem 61 is set to a first gain value of $g_{mwave}$ by the controller 63. The algorithm then continues with process step 218, in which the nerve 50 is stimulated with the previously determined stimulation magnitude. Immediately thereafter, in process step 220, the evoked muscle response is acquired by the controller 63 for a first predetermined amount of time, $t_{mwave}$.

The first gain of the signal conditioning system, $g_{mwave}$, can be predetermined or dynamically established. The predetermined value is between about 500 and about 8000, and is preferably about 2000, based on an empirical analysis of a many signals. The system can also dynamically determine the gain by incrementally increasing the gain, under control by the controller 63, until the amplified response generated by the signal conditioning subsystem 61 saturates the analog-to-digital acquisition circuit of the controller 63.

The value of $t_{mwave}$ must be sufficient to ensure that normal and prolonged pathological M-waves are captured. In one comprehensive study of the distal motor latency in subjects with Carpal Tunnel Syndrome, the mean distal motor latency was found to be 4.94±1.03 milliseconds. (See Kimura, "The Carpal Tunnel Syndrome: Localization of Conduction Abnormalities within the Distal Segment of the median Nerve", *Brain*, 102:619–635 (1979)). In this study, 99% of the subjects had a DML of 8 milliseconds or less. Thus, $t_{mwave}$ is set at about 10 milliseconds to about 30 milliseconds, and is preferably about 12.8 milliseconds. This ensures that all pathological signals will be acquired and that, even in those severely pathological signals (e.g., DML>7 milliseconds), a sufficient portion of the M-wave will be recorded for waveform analysis purposes (e.g., at least 5 milliseconds).

Immediately after completing process step 220, the algorithm continues with process step 194, in which the gain of the signal conditioning subsystem 61 is set to a second gain value of $f_{mwave}$ by the controller. The algorithm then continues with process step 226, in which the output from the signal conditioning subsystem 61 is acquired for a predetermined amount of time, $t_{fwave}$, starting a predetermined amount of time, $t_{offset}$, after the onset of the stimulus.

The second gain of the signal conditioning system, $f_{mwave}$, is predetermined and is between about 10,000 and about 30,000, and is preferably about 15,000. This value is based on an empirical analysis of a many signals. The values of $t_{offset}$ and $t_{fwave}$ are predetermined according to the known values of F-wave latencies in the literature. Normal subjects typically have F-wave latencies of 26.6±2.2 milliseconds (See, e.g., *Electrodiagnosis in Diseases of Nerve and Muscle: Principles and Practice*, 1989, Ed. J. Kimura). Therefore, 99% of patients have a F-wave latencies greater than 20 milliseconds. Thus, $t_{offset}$ is set at this value. The value of $t_{fwave}$ is then set at 32 milliseconds, which will capture the majority of pathological F-wave latencies (See, e.g., Kimura, *Principles and Practice*, supra) and utilizes a reasonable amount of memory.

Upon completion of process step 226, the algorithm immediately proceeds to process step 228, in which the mean absolute deviation of the signal, $\phi_i$, is calculated in a manner similar to that described above for the absolute deviation of the noise. This value is used to determine the noise dependent threshold utilized in the aforementioned algorithm for identifying the F-wave latency 208.

Upon completing process step 228, the algorithm continues with process step 230, in which the signal acquired during the $t_{mwave}$ portion is processed to yield a DML, as described above. The algorithm then determines the F-wave latency in process step 232 using the approach described above. Finally, in process step 234, the algorithm compares the stimulation counter against a predetermined limit, max$_{stim}$. If the stimulation counter, i, is not equal to this limit then the algorithm proceeds to process step 216, which restarts the nerve stimulation and acquisition sequence. If the stimulation counter, i, is equal to the limit, max$_{stim}$, the algorithm proceeds to process step 238, in which the mean DML is calculated. The algorithm then proceeds to process step 240, in which the median F-wave latency is calculated. Both of these calculated values (DML and F-wave latency) are corrected for variations in skin temperature in process step 242 using the equations described below.

$$dml_{corrected} = dml_{raw} + (T-T_0)k_{dml}$$

$$fwave_{corrected} = fwave_{raw} + (T-T_0)k_{fwave}$$

where T is the skin surface temperature as measured by the temperature sensor 36, $k_{dml}$ is a temperature correction factor for the distal motor latency derived from the neurological literature (See, e.g., Electrodiagnosis in Diseases of Nerve and Muscle: Principles and Practice, 1989, Ed. J. Kimura), $k_{fwave}$ is a temperature correction factor for the F-wave latency derived from the neurological literature (See, e.g., Kimura, *Principles and Practice*, supra), and $T_0$ is the desired temperature to which the mean DML and median F-wave latency are corrected. $T_0$ is between about 30° C. and about 34° C., and is preferably about 32° C. Finally, these corrected values are displayed in process step 244. Subsequently, the algorithm returns to process step 202 and waits for reactivation of the START switch S1.

An important object of the present invention is to provide the operator with neuromuscular parameters that are accurate and reproducible. For example, as has been described above, the DML and the F-wave latency are corrected for variations in the skin surface temperature as measured by the temperature sensor 36 embedded within the neuromuscular electrode 1. Additional factors that impact the accuracy of neuromuscular diagnostic parameters are the height and age of the test subject. In a preferred embodiment, the DML and F-wave latency are automatically adjusted by the controller 63 to account for the height and age according to the following equations.

$$dml_{height\_age\_corrected} = \frac{-1}{\frac{-1}{dml_{temperature\_corrected}} + (A_0 - A)h_{dml} + (H_o - H)h_{dml}}$$

$$fwave_{height\_age\_corrected} = \frac{-1}{\frac{-1}{fwave_{temperature\_corrected}} + (A_0 - A)h_{fwave} + (H_o - H)h_{fwavel}}$$

where H is the height of the test subject in centimeters, $H_0$ is the normalized height in centimeters to which the DML and F-wave values are corrected, A is the age of the test subject in years, $A_0$ is the normalized age in years to which the DML and F-wave values are corrected, $h_{dml}$ and $a_{dml}$ are height and age correction factors, respectively, for the distal motor latency derived from the neurological literature (See, e.g., Stetson, et al., "Effects of Age, Sex, and Anthropometric Factors on Nerve Conduction Measures," *Muscle & Nerve*, 15:1095–1104 (1992)), and $h_{fwave}$ and $a_{fwave}$ are height and age correction factors, respectively, for the F-wave latency derived from the neurological literature (See, e.g., Stetson, supra). Furthermore, other height and age correction equations have been contemplated and should be considered within the scope of the present invention. Additionally, correction of the conduction velocity by equations similar to those provided above is well known to those of ordinary skill in the art.

In the preferred embodiment, the approximate height of the test subject is automatically derived from the size of the neuromuscular electrode 1 used. In particular, the height is obtained by reading the two bits within the EEPROM in the temperature sensor 36, which encodes the size of the neuromuscular electrode 1, as described above, and then translating that size into a height using Table 1.

TABLE 1

| EEPROM | Size | Height (in centimeters) |
|---|---|---|
| 00 | Small (4.028 in) | 161.8 |
| 01 | Medium (4.308 in) | 172 |
| 10 | Large (4.579 in) | 180.9 |

In other embodiments, the height of the test subject can be entered into the monitor 2 using user actuable controls 65 or the external interface 67.

Although the illustrative algorithms described above pertain to the detection of CTS, the apparatus of the present invention may used to detect other forms of nerve disease and to evaluate neuromuscular blockade. For example, the train-of-four (TOF) protocol, which is commonly used to evaluate the degree of neuromuscular blockade in anesthetized patients, is readily implemented using an apparatus of the invention. In particular, a predetermined number (usually four) of muscle responses 120 are evoked at a predetermined rate (e.g., 2 Hz) and the amplitude 126 of each response determined. Subsequently, the ratio of the amplitude of the last of the plurality of muscle responses to be evoked is divided by the amplitude of the first of the plurality of muscle responses to be evoked. This ratio is recognized as a sensitive indicator of neuromuscular blockade.

The aforementioned algorithms are intended for illustrative purposes only. Other algorithms may be developed which detect CTS or diabetic neuropathy using an apparatus of the invention. For example, parameters other than the DML, F-wave latency, and conduction velocity may be incorporated into the diagnostic algorithms. Illustrative parameters include: waveform features of the evoked muscle response 120, such as, for example, the amplitude and width. Additional illustrative parameters include waveform features of processed forms of the evoked muscle response 120, such as, for example, its derivatives, its Fourier transform, and other parameters derived from statistical analyses (e.g., principal component analysis). Furthermore, additional parameters are obtained by comparison of any of the above parameters at different stimulation levels.

Another algorithm of the invention is for ensuring that the neuromuscular 1 is not reused, for the reasons enumerated above. In this algorithm, an electronic flag (i.e., a single bit) within the EEPROM of temperature sensor 36 is utilized. In particular, once a test is initiated, such as by pressing the START switch S1, the status of the electronic flag is checked. If the flag is clear (i.e., the appropriate bit is 0), the monitor 2 proceeds with the test. If the electronic flag is set (i.e., the appropriate bit is 1), the monitor 2 does not proceed and instead indicates, such as with indicator 66, that the user is attempting to perform a test with an inactivated neuromuscular electrode 1. It is important to note that the electronic flag is always cleared during manufacturing of the neuromuscular electrodes 1, so the neuromuscular electrode always has a cleared (i.e., the appropriate bit is 0) electronic flag upon first use.

In one algorithm, the neuromuscular electrode 1 must be inactivated through setting of the electronic flag upon its removal from the skin after use. This may be accomplished in a number of different ways. In one embodiment, the impedance between any two among the plurality of electrodes 21, 22, 30, 31, 27 within the neuromuscular electrode 1 is monitored at a frequent and predetermined rate (such as for example, every second). Removal of the neuromuscular electrode 1 from, for example, the subject's forearm 8 is detected when the impedance exceeds a predetermined level, which is preferably greater than 1 MΩ. In another embodiment, the signal from the signal conditioning subsystem 61 is continuously monitored by the controller 63. When the neuromuscular electrode 1 is removed from the forearm 8, the inputs to the differential amplifier 60 float causing certain detectable characteristics of the signal to change. These characteristics include the DC offset and the power spectrum. In yet another embodiment, certain predetermined characteristics of the evoked muscle response 120 are monitored and compared against previous tests in the same neuromuscular electrode 1. The identity of the neuromuscular electrode 1 is established by the unique serial number, as stored in data memory of temperature sensor 36. If these characteristics are found to change to a significant degree, the test is halted and the electronic flag is set, thus inactivating the neuromuscular electrode 1. A particularly effective muscle response 120 characteristic is the polarity of the signal, which is quantified by the amplitude (e.g., positive or negative) of the peak 126. A switch in the polarity of the muscle response 120 indicates that neuromuscular electrode 1 has been moved from one hand to the other.

An additional object of the present invention is to ensure that neuromuscular diagnostic information obtained with the disclosed apparatus and methods is correctly associated with the test subject. In a preferred embodiment, the unique serial number embedded within the data memory of neuromuscular electrode 1 is read by the monitor 2 and associated with the display, such as with indicator 66, or other output though the external interface 67, of test results such as the DML and F-wave latency. For example, the external interface 67 may be connected to a modem that transmits the DML, F-wave latency and associated waveforms to a remote information service. In a preferred embodiment, the data is tagged, or otherwise associated, with the unique serial number 36 embedded in the data memory of neuromuscular electrode 1 used to obtain the data. Furthermore, in the preferred embodiment, the operator is directed to attach the previously described labels that have the same unique serial number printed on them to the test subject's chart. As a result, the test subject's chart and his neuromuscular diagnostic information, stored on the remote information service, are robustly linked.

The disclosed invention provides a new approach to monitoring neuromuscular physiology. Apparatus and methods are described for the substantially automated and highly efficient measurement of many different parameters of neuromuscular physiology. These indicators may be used to detect CTS and other peripheral nerve diseases, such as diabetic neuropathy, as well as to monitor neuromuscular blockade caused by pathological, pharmacological and chemical means. The invention possesses the significant advantage that, unlike conventional measurements of nerve conduction across the wrist, the disclosed invention provides for a single integrated neuromuscular electrode that is placed immediately proximal to the wrist (i.e., the wrist crease). Alternatively, the neuromuscular electrode is placed at or proximal to the ankle joint. These are very familiar anatomic locations, so the placement operation is rapidly and easily undertaken by most adults. Unlike apparatus and methods of the prior art, the disclosed invention does not require placement of multiple sets of electrodes on both sides of the wrist, which is a difficult and error prone procedure for non-experts. An additional advantage of the disclosed invention emerges from the fact that the integrated neuromuscular electrode may be manufactured as a low-cost, disposable item. Consequently, the possibility of cross-contamination among users of the apparatus is significantly reduced. Furthermore, the low-cost, and ease of use will promote frequent monitoring of neuromuscular disorders, such as CTS and diabetic neuropathy, providing the potential benefits of early detection and regular tracking of these diseases. Another advantage of the present invention is that the process of evoking, detecting and processing neuromuscular signals is carried out in an entirely automated fashion, without requiring involvement of either the user of the apparatus or trained personnel. A further advantage of the present invention is that the smallest and fewest electrical stimuli consistent with an accurate diagnostic assessment are used. As a result, discomfort to the user is minimized and, in most cases, eliminated entirely.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereinafter claimed. Accordingly, the scope of the invention is limited only by the scope of the appended claims.

What claimed is:

1. A method of assessing a physiological function detectable in an arm and a hand of an individual, comprising the steps of:

(a) applying a stimulus proximal to a wrist of an individual, whereby application of said stimulus stimulates a nerve that traverses said wrist and thereby generates an impulse that is conducted by said nerve;

(b) detecting a myoelectric potential proximal to said wrist of said individual, whereby said myoelectric potential is generated by a muscle in said hand of said individual in response to said impulse, said muscle being in communication with said nerve and said impulse being conducted to said muscle after propagation of said impulse through a spinal cord of said individual;

(c) processing said stimulus and said myoelectric potential; and (d) correlating said processing results to a physiological function of a peripheral nervous system of said individual.

2. The method of claim 1, further comprising the step of removing a trend from a baseline of said myoelectric potential.

3. The method of claim 2, wherein said removing step comprises the steps of:

(a) determining a straight line fit of said myoelectric potential; and (b) subtracting said straight line from said myoelectric potential.

4. The method of claim 2, wherein said removing step comprises the steps of:

(a) detecting a plurality of myoelectric potentials;

(b) averaging said plurality of myoelectric potentials; and (c) subtracting said average from each of said plurality of myoelectric potentials.

5. The method of claim 4, further comprising the steps of:

(a) determining a first derivative for each of said myoelectric potentials, thereby to obtain a plurality of first derivatives;

(b) determining a mean of said plurality of first derivatives;

(c) determining a statistical distribution of said plurality of first derivatives; and (d) removing from said plurality of myoelectric potentials that are averaged in step (b) of claim 4 any segment of a myoelectric potential of said plurality of myoelectric potentials that has a first derivative removed by a predetermined factor from said mean of said derivatives.

6. The method of claim 1, farther comprising the step of filtering said myoelectric potential.

7. The method of claim 6, wherein said filtering step comprises digitally filtering said myoelectric potential.

8. The method of claim 1, wherein said physiological function comprises a F-wave latency between application of said stimulus and detection of said myoelectric potential and wherein said processing step further comprises the step of determining said F-wave latency and said correlating step further comprises the step of producing an indicia of said F-wave latency.

9. The method of claim 8, wherein said step of determining a F-wave latency comprises the steps of:
   (a) detecting an F-wave response signal in said myoelectric potential;
   (b) determining a maximum peak of said F-wave response signal;
   (c) identifying a first minimum peak and a second minimum peak of said F-wave response signal, both of said first and second minimum peaks being adjacent said maximum peak of said F-wave response signal;
   (e) determining an amplitude of said maximum peak of said F-wave response signal to one of said first and second minimum peaks of said F-wave response signal;
   (f) determining a noise dependent threshold;
   (g) comparing said amplitude to said noise dependent threshold; and
   (h) determining a F-wave latency when said amplitude is greater than or equal to said noise dependent threshold.

10. The method of claim 9, wherein said step of determining a maximum peak of said F-wave response signal comprises determining a portion of said myoelectric potential for which a first derivative of said myoelectric potential is equal to zero.

11. The method of claim 9, wherein said step of identifying first and second minimum peaks of said F-wave response signal comprises determining a portion of said myoelectric potential for which a first derivative of said myoelectric potential is equal to zero.

12. The method of claim 9, wherein said step of determining a noise dependent threshold comprises the steps of:
   (a) determining a level of noise after detecting said myoelectric potential; and
   (b) multiplying said level of noise by a predetermined factor.

13. The method of claim 9, wherein said step of determining a noise dependent threshold, comprises the steps of:
   (a) determining a level of noise before detecting said myoelectric potential; and
   (b) multiplying said level of noise by a predetermined factor.

14. The method of claim 9, wherein said step of determining a F-wave latency comprises the step of identifying an inflection of said myoelectric potential, said inflection preceding said maximum peak of said F-wave response signal.

15. The method of claim 14, wherein said inflection comprises a point on said myoelectric potential having a first derivative less than or equal to zero.

16. The method of claim 14, wherein said inflection comprises a minimum peak of a first derivative of said myoelectric potential.

17. The method of claim 9, further comprising the step of processing atypical waveform shapes in said F-wave response signal.

18. The method of claim 17, wherein said step of processing atypical waveform shapes comprises the steps of:
   (a) determining a location of a minimum peak of said F-wave response signal;
   (b) inverting said F-wave response signal; and
   (c) assigning a maximum peak of said inverted F-wave response signal to said location of said minimum peak of said F-wave response signal.

19. The method of claim 9, further comprising the step of confirming said F-wave latency.

20. The method of claim 19, wherein said step of confirming said F-wave latency comprises the steps of:
   (a) determining a first derivative of said myoelectric potential at a plurality of points within a first time period preceding said F-wave latency, thereby obtaining a plurality of first derivatives within said first time period;
   (b) averaging said plurality of first derivatives within said first time period; and
   (c) comparing said average with a maximum peak and a minimum peak of said F-wave response signal in a second time period following said F-wave latency.

21. The method of claim 19, wherein said step of confirming said F-wave latency comprises the steps of:
   (a) identifying a maximum or minimum peak in said myoelectric potential at a point of said myoelectric potential that precedes said F-wave latency; and
   (b) comparing said identified peak to said maximum peak of said F-wave response signal.

22. The method of claim 8, further comprising the step of indicating said F-wave latency in response to said indicia.

23. The method of claim 8, further comprising the step of producing a signal indicative of a peripheral nervous system disorder in response to said F-wave latency.

24. The method of claim 23, further comprising the step of indicating a peripheral nervous system disorder in response to said signal.

25. The method of claim 8, further comprising the steps of measuring a skin temperature of said arm of said individual and modifying said F-wave latency in response thereto.

26. The method of claim 8, further comprising the steps of determining a height of said individual and modifying said F-wave latency in response thereto.

27. The method of claim 8, further comprising the steps of determining an age of said individual and modifying said F-wave latency in response thereto.

28. A method of assessing a physiological function of a leg and a foot of an individual, comprising the steps of:
   (a) applying a stimulus proximal to an ankle joint of an individual, whereby application of said stimulus stimulates a nerve that traverses said ankle joint and thereby generates an impulse that is conducted by said nerve;
   (b) detecting a myoelectric potential proximal to said ankle joint of said individual, whereby said myoelectric potential is generated by a muscle in said foot of said individual in response to said impulse, said muscle being in communication with said nerve and said impulse being conducted to said muscle after propagation of said impulse through a spinal cord of said individual;
   (c) processing said stimulus and said myoelectric potential; and
   (d) correlating said processing results to a physiological function of a peripheral nervous system of said individual.

29. The method of claim 28, further comprising the step of removing a trend from a baseline of said myoelectric potential.

30. The method of claim 29, wherein said removing step comprises the steps of:
   (a) determining a straight line fit of said myoelectric potential; and
   (b) subtracting said straight line from said myoelectric potential.

31. The method of claim 29, wherein said removing step comprises the steps of:
   (a) detecting a plurality of myoelectric potentials;
   (b) averaging said plurality of myoelectric potentials; and (c) subtracting said average from each of said plurality of myoelectric potentials.

32. The method of claim 31, further comprising the steps of:
(a) determining a first derivative for each of said myoelectric potentials, thereby to obtain a plurality of first derivatives;
(b) determining a mean of said plurality of first derivatives;
(c) determining a statistical distribution of said plurality of first derivatives; and
(d) removing from said plurality of myoelectric potentials that are averaged in step (b) of claim 31 any segment of a myoelectric potential of said plurality of myoelectric potentials that has a first derivative removed by a predetermined factor from said mean of said derivatives.

33. The method of claim 28, further comprising the step of filtering said myoelectric potential.

34. The method of claim 33, wherein said filtering step comprises digitally filtering said myoelectric potential.

35. The method of claim 28, wherein said physiological function comprises a F-wave latency between application of said stimulus and detection of said myoelectric potential and wherein said processing step further comprises the step of determining said F-wave latency and said correlating step further comprises the step of producing an indicia of said F-wave latency.

36. The method of claim 35, wherein said step of determining a F-wave latency comprises the steps of:
(a) detecting an F-wave response signal in said myoelectric potential;
(b) determining a maximum peak of said F-wave response signal;
(c) identifying a first minimum peak and a second minimum peak of said F-wave response signal, both of said first and second minimum peaks being adjacent said maximum peak of said F-wave response signal;
(e) determining an amplitude of said maximum peak of said F-wave response signal to one of said first and second minimum peaks of said F-wave response signal;
(f) determining a noise dependent threshold;
(g) comparing said amplitude to said noise dependent threshold; and
(h) determining a F-wave latency when said amplitude is greater than or equal to said noise dependent threshold.

37. The method of claim 36, wherein said step of determining a maximum peak of said F-wave response signal comprises determining a portion of said myoelectric potential for which a first derivative of said myoelectric potential is equal to zero.

38. The method of claim 36, wherein said step of identifying first and second minimum peaks of said F-wave response signal comprises determining a portion of said myoelectric potential for which a first derivative of said myoelectric potential is equal to zero.

39. The method of claim 36, wherein said step of determining a noise dependent threshold comprises the steps of:
(a) determining a level of noise after detecting said myoelectric potential; and
(b) multiplying said level of noise by a predetermined factor.

40. The method of claim 36, wherein said step of determining a noise dependent threshold, comprises the steps of:
(a) determining a level of noise before detecting said myoelectric potential; and
(b) multiplying said level of noise by a predetermined factor.

41. The method of claim 36, wherein said step of determining a F-wave latency comprises the step of identifying an inflection of said myoelectric potential, said inflection preceding said maximum peak of said F-wave response signal.

42. The method of claim 41, wherein said inflection comprises a point on said myoelectric potential having a first derivative less than or equal to zero.

43. The method of claim 41, wherein said inflection comprises a minimum peak of a first derivative of said myoelectric potential.

44. The method of claim 36, further comprising the step of processing atypical waveform shapes in said F-wave response signal.

45. The method of claim 44, wherein said step of processing atypical waveform shapes comprises the steps of:
(a) determining a location of a minimum peak of said F-wave response signal;
(b) inverting said F-wave response signal; and
(c) assigning a maximum peak of said inverted F-wave response signal to said location of said minimum peak of said F-wave response signal.

46. The method of claim 36, further comprising the step of confirming said F-wave latency.

47. The method of claim 46, wherein said step of confirming said F-wave latency comprises the steps of:
(a) determining a first derivative of said myoelectric potential at a plurality of points within a first time period preceding said F-wave latency, thereby obtaining a plurality of first derivatives within said first time period;
(b) averaging said plurality of first derivatives within said first time period; and
(c) comparing said average with a maximum peak and a minimum peak of said F-wave response signal in a second time period following said F-wave latency.

48. The method of claim 46, wherein said step of confirming said F-wave latency comprises the steps of:
(a) identifying a maximum or minimum peak in said myoelectric potential at a point of said myoelectric potential that precedes said F-wave latency; and
(b) comparing said identified peak to said maximum peak of said F-wave response signal.

49. The method of claim 35, further comprising the step of indicating said F-wave latency in response to said indicia.

50. The method of claim 35, further comprising the step of producing a signal indicative of the presence or absence of diabetic neuropathy in response to said F-wave latency.

51. The method of claim 50, further comprising the step of indicating the presence or absence of diabetic neuropathy in response to said signal.

52. The method of claim 35, further comprising the steps of measuring a skin temperature of said leg of said individual and modifying said F-wave latency in response thereto.

53. The method of claim 35, further comprising the steps of determining a height of said individual and modifying said F-wave latency in response thereto.

54. The method of claim 35, further comprising the steps of determining an age of said individual and modifying said F-wave latency in response thereto.

* * * * *